United States Patent [19]

Tajima et al.

[11] Patent Number: 5,637,309
[45] Date of Patent: Jun. 10, 1997

[54] PHYSIOLOGICALLY ACTIVE SUBSTANCE-PROLONGED RELEASING-TYPE PHARMACEUTICAL PREPARATION

[75] Inventors: Masahiro Tajima, Yokohama; Takashi Yoshimoto, Sendai; Shoji Fukushima; Toshihiko Kaminuma, both of Yokohama; Ritsuko Ehama, Tokyo; Takaaki Baba; Kazuo Watabe, both of Yokohama, all of Japan

[73] Assignee: Shiseido Company, Ltd., Tokyo, Japan

[21] Appl. No.: 309,152

[22] Filed: Sep. 20, 1994

[30] Foreign Application Priority Data

| Sep. 20, 1993 | [JP] | Japan | 5-265340 |
| Sep. 20, 1993 | [JP] | Japan | 5-265341 |
| Sep. 20, 1993 | [JP] | Japan | 5-265342 |
| Dec. 17, 1993 | [JP] | Japan | 5-344275 |
| Jan. 27, 1994 | [JP] | Japan | 6-036254 |
| Feb. 14, 1994 | [JP] | Japan | 6-050953 |

[51] Int. Cl.⁶ .................... A61F 2/00; A61K 9/20
[52] U.S. Cl. .................. 424/423; 424/457; 424/468; 424/426; 514/772.3; 514/777; 514/781; 514/784; 514/785; 514/808; 514/929
[58] Field of Search ............. 424/457, 468, 424/422, 423, 426; 514/772.3, 777, 781, 784, 785, 808, 929

[56] References Cited

U.S. PATENT DOCUMENTS

| 4,882,167 | 11/1989 | Jang | 424/468 |
| 5,112,614 | 5/1992 | Magruder et al. | 424/422 |
| 5,236,908 | 8/1993 | Gruber et al. | 514/46 |
| 5,252,318 | 10/1993 | Joshi et al. | 424/78.04 |
| 5,356,629 | 10/1994 | Sander et al. | 424/422 |

FOREIGN PATENT DOCUMENTS

| 0196700 | 10/1986 | European Pat. Off. . |
| 0211266 | 2/1987 | European Pat. Off. . |
| 0255404 | 2/1988 | European Pat. Off. . |
| 0309100A2 | 3/1989 | European Pat. Off. . |
| 89/03686 | 5/1989 | WIPO . |
| 91/00293 | 1/1991 | WIPO . |

OTHER PUBLICATIONS

Park et al., "Biodegradable Hydrogels for Drug Delivery", pp. 211–212 (1993).

Lerner et al., "Isolation of Maxadilan, a Potent Vasodilatory Peptide from the Salivary Glands of the Sand Fly *Lutzomyia longipalpis*", The Journal of Biological Chemistry, vol. 266, No. 17, Jun. 15, 1991, pp. 11234–11236.

Lerner et al., J. Biol. Chem., "Maxadilan: Cloning and Functional Expression of the Gene Encoding This Potent Vasodilator Peptide", vol. 267, pp. 1062–1066 (Jan. 15, 1992).

Ohnuma et al., Peptide Chemistry 1993 "Vasodilatory Peptide 'Maxadilan'", Okada (Ed.) pp. 145–148 (1993).

Shimizu et al., Nou Shinkei Geka (Neurosurgery) 22(2): 131–139 (Feb. 1994) and partial translation.

*Primary Examiner*—Thurman K. Page
*Assistant Examiner*—James M. Spear
*Attorney, Agent, or Firm*—Wenderoth, Lind & Ponack

[57] ABSTRACT

A prolonged releasing pharmaceutical preparation is provided carrying a physiologically active substance, particularly, calcitonin gene-related peptide (CGRP) or a maxadilan (MAX). This pharmaceutical preparation can attain the expected effects by incorporating the physiologically active substance into a combination, as carriers for the physiologically active substance, of a cellulosic polymer and at least one auxiliary component selected from the group consisting of fats and oils, waxes, fatty acids, saccharides and polyacrylate ester derivatives. The pharmaceutical preparation can conveniently be used, in living bodies, particularly as an intrathecal implantation-type preparation.

26 Claims, 16 Drawing Sheets

PHYSIOLOGICALLY ACTIVE SUBSTANCE-PROLONGED RELEASING-TYPE PHARMACEUTICAL PREPARATION

BACKGROUND OF THE INVENTION

1. Field of the Invention

This invention relates to a pharmaceutical preparation capable of prolonged releasing a physiologically active substance in a controlled state. The pharmaceutical preparation is, particularly, directed to physiologically active peptides such as calcitonin gene-related peptide (CGRP) and maxadilans (MAXs). The pharmaceutical preparation of the invention is useful as an intracorporeal implantation-type, particularly intrathecal implantation-type physiologically active substance-prolonged releasing preparation.

2. Description of Related Art

Prolonged releasing (hereinafter, the same as gradually or delayed releasing) preparations, wherein the drugs or physiologically active substances are administered into living bodies, elution of the drugs in the living bodies is controlled and their absorption is adjusted, have been investigated from long ago. For example, a method which comprises coating drugs with various coats, a method which comprises incorporating drugs into matrices of waxes or macromolecules, etc. have been known.

However, when intrathecal diseases are treated, in the case of intravenous administration of physiologically active substances, migration of these physiologically active substances into the brains is prevented by the blood brain barriers. As a method for direct administration of a physiologically active substance into brains, there is a method which comprises seating a catheter at the time of the operation and gradually supplying the drug into the brain, but since the apparatus is expensive and in addition there is a large danger of infection, it is hard to say that the method is a reliable method. For example, in delayed cerebral vasospasm occurring after subarachnoid hemorrhage, the pathosis is retardingly manifested and moreover is lasting, and thus a method which comprises inserting a catheter for administration of drugs and a method which comprises continuously administering a drug into the vein are used. However, it is the present state of things that a method for obtaining sure therapeutic effects has not yet been developed.

When one's eyes are turned to physiologically active peptides, particularly calcitonin gene-related peptide (CGRP) and maxadilans (MAXs) about which the present inventors have contemplated development of pharmaceutical preparations effective for various diseases, prolonged releasing pharmaceutical preparations for active substances specifically effective in relation to targeted diseases have not been proposed. When CGRP and maxadilans are specifically taken up, these are extremely interesting as proteins capable of inducing vasodilative and temporary immune suppression in mammals, as disclosed in E. A. Lerner et al., International Publication No. WO 91/00293, but after the report of Lerner et al., prolonged releasing pharmaceutical preparations therefor have not been proposed.

In this connection, the "maxadilans" were described in the above publication as proteins derived from the salivary gland lysate of a sand fly *Lutzomyia longipalpis*, and, thereafter, named "maxadilans" by them (for example, *J. Biol. Chem.*, vol. 267, 1062–1066, 1992). Lerner et al. exhibit, in the just above literature, through expression of recombinant maxadilans, that the analogues of maxadilan disclosed in WO 91/00293 also have a vasodilative activity.

Other maxadilan analogues having a vasodilative activity are disclosed in M. Ohnuma, E. A. Lerner et al., Peptide Chemistry 1993: Y. Okada (Ed.), 145–148.

As an interesting report from the aspect of the pharmacological actions of CGRP, H. Shimizu et al., Nou Shinkei Geka (Neurosurgery), 22(2): 131–139, 1994 discloses that when subarachnoid hemorrhage models of rabbits are used, and portions of an aseptic solution of CGRP (human alpha CGRP: Bachem Feinchemikalien, AG, Budendorf, Switzerland) are injected into the cisterna magnas of the animals, respectively, dilation effects on the contracted blood vessels are obtained.

However, this method is not always satisfactory in the effects of prophylaxis or treatment of cerebral vasospasm where the pathosis is retardingly manifested as stated above, and moreover, it is necessary to continue to strictly monitor the injection of the aqueous solution of the physiologically active substance into the cisterna magna, since said injection is very dangerous, during the injection operation.

Thus, the object of this invention lies in providing a pharmaceutical preparation effective for prophylaxis or treatment of, especially cerebral vasospasm, and a method therefor.

SUMMARY OF THE INVENTION

The present inventors, in order to accomplish the above object, have investigated above combinations of the contemplated physiologically active substances with various carriers, and have found, unexpectedly, that when a cellulosic polymer-based carrier is used, the physiologically active substance, particularly the physiologically active peptide exhibits controlled releasability. As a further result of this research, they also found that MAXs themselves are effective for prophylaxis and treatment of cerebral vasospasm, irrespective of their dosage forms.

Another important finding found by the present inventors is that a method to implant a prolonged releasing pharmaceutical preparation containing a compound having a vasodilative action into the brain, which method has hitherto not been tried at all as a method to present or treat cerebral vasospasm, and has not been disclosed nor suggested in scientific literatures, etc., is extremely effective for prophylaxis or treatment of the disease.

Thus, this invention is directed to a pharmaceutical preparation carrying an effective amount of a physiologically active substance and capable of prolonged releasing the physiologically active substance, wherein the carrier of the physiologically active substance comprises a combination of a cellulosic polymer and at least one auxiliary component selected from fats and oils, waxes, fatty acids, saccharides and polyacrylate ester derivatives.

As a more specific embodiment, this invention is directed to a pharmaceutical preparation carrying an effective amount of a physiologically active substance and capable of prolonged releasing the physiologically active substance, wherein the physiologically active substance is one or more selected from the group consisting of CGRP and MAXs, and the carrier of the physiologically active substance comprises 10 to 90% by weight of a cellulose ether derivative, 1 to 30% by weight of a fat or oil or a wax, and 1 to 30% by weight of a fatty acid, based on the total weight of the pharmaceutical preparation; or the carrier of the physiologically active substance comprises 10 to 90% by weight of a cellulose ether derivative and 1 to 40% by weight of a saccharide, based on the total weight of the pharmaceutical preparation; or the carrier of the physiologically active substance is a combination of 10 to 90% by weight of crystalline cellulose and 0.01 to 10% by weight of a polyacrylate ester derivative with at least one or more selected from the group consisting of 1 to 30% by weight of a fatty acid, 1 to 30% by weight of a fat or an oil and 1 to 30% by weight of a wax, based on the total weight of the pharmaceutical preparation; or the carrier of the physiologically active substance comprises about 50% by weight of hyaluronic acid and about 50% by weight of a cationic polyacrylic acid derivative, based on the total weight of the pharmaceutical preparation.

As still another embodiment, this invention is directed to a method for prophylaxis or treatment of cerebral vasospasm which comprises administering an effective amount of at least one of MAXs into the body.

As still another embodiment, this invention is directed to a method for prophylaxis or treatment of cerebral vasospasm by use of a compound having a vasodilative action as a physiologically active substance, which comprises a step to implant a prolonged releasing (gradually releasing) pharmaceutical preparation carrying the compound into the brain.

As still another embodiment, this invention is directed to the use of a compound having a vasodilative action for preparing an intrathecal implantation-type prolonged releasing pharmaceutical preparation for prophylaxis or treatment of cerebral vasospasm.

DETAILED DESCRIPTION OF THE INVENTION

Figure 1:
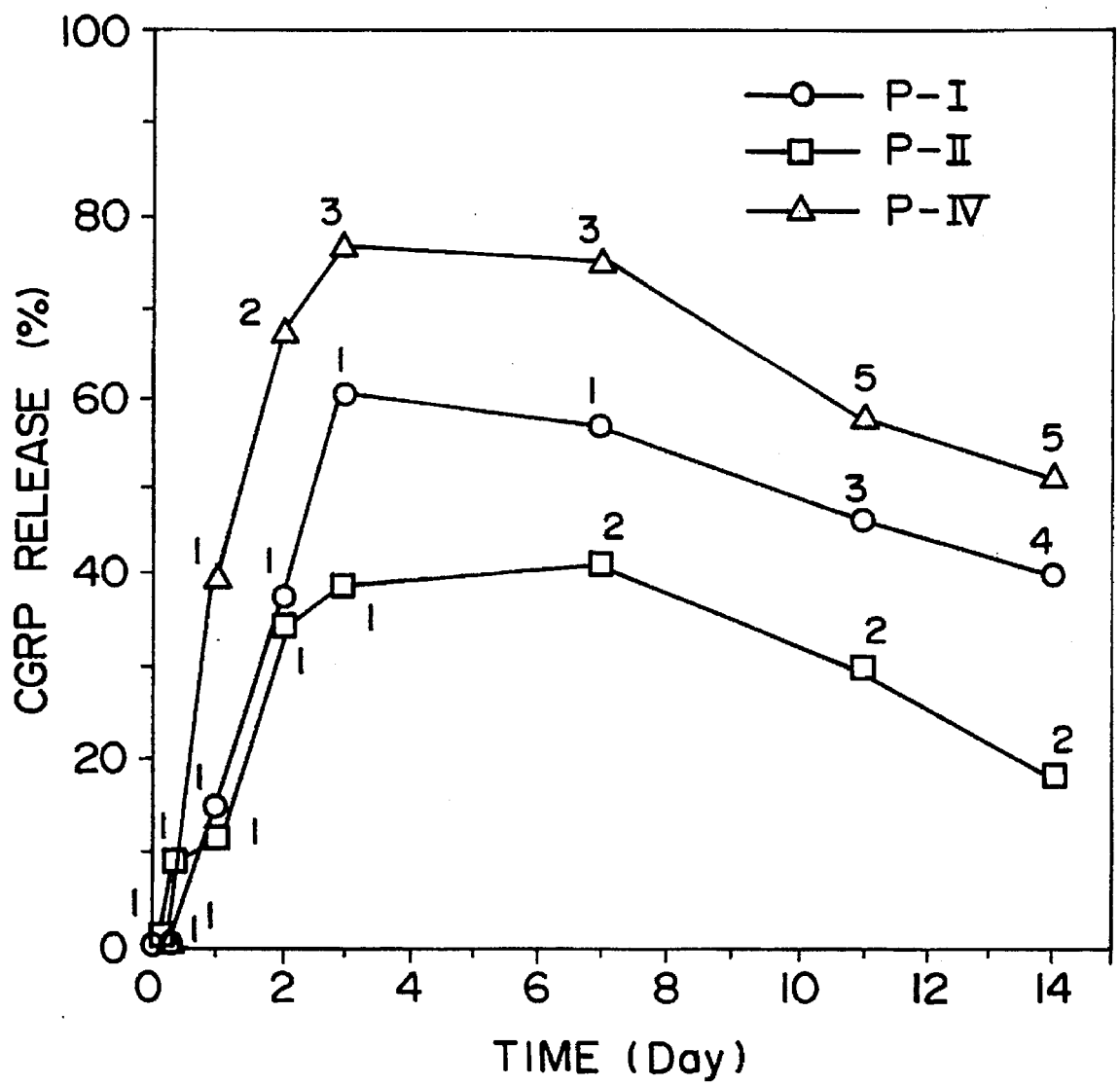
FIG. 1 is a graph showing the behaviors of release of CGRP from pharmaceutical preparation of the invention, P-I, P-II and P-III (prepared in Example 1, Example 2 and Example 3, respectively) in the in vitro test.

Cellulosic polymers used in the invention include, for example, cellulose ether derivatives such as hydroxypropylcellulose, methylcellulose, hydroxypropylmethylcellulose, hydroxyethylcellulose and carboxymethylcellulose; and crystalline cellulose. Preferred among the cellulose ether derivatives is hydroxypropylcellulose. The compounding amount of this polymer in the pharmaceutical preparation cannot be limited since it varies depending on the kinds of auxiliaries to be combined and physiologically active substances to be carried thereon, and is determined taking release initiation time and release sustainment time into account, but is generally 10 to 90% by weight, preferably 40 to 60% by weight, based on the total weight of the pharmaceutical preparation.

Fat and oils or waxes include hardened oils, cacao butter, beef tallow, lard, beeswax, carnauba wax, white wax, etc. Preferred among them are hardened oils. The compounding amount thereof is not limitative, either, and can be determined taking release initiation time and release sustainment time into account, but is generally 1 to 30% by weight, preferably 10 to 20% by weight, based on the total weight of the pharmaceutical preparation. Hereafter, expressions of % by weight are based on the total weights of the pharmaceutical preparations, respectively, unless otherwise defined.

Fatty acids include saturated or unsaturated carboxylic acids having 12 to 22 carbon atoms such as stearic acid, lauric acid, myristic acid, isostearic acid, palmitic acid and behenic acid. Stearic acid is preferred among them. The compounding amount thereof is not limitative, and can also be determined taking release initiation time and release sustainment time into account, but is generally 1 to 30% by weight, preferably 10 to 20% by weight.

Saccharides include sucrose, lactose, glucose, fructose, maltose, dextrin, trehalose, pullulan, etc. Preferred among them are lactose and glucose. The disintegrability of the gradually releasing preparation can be adjusted by addition of a saccharide. Namely, the disintegration velocity can be accelerated by increasing its compounding amount. The compounding amount is not limitative, and can also be determined taking release initiation time and release sustainment time into account, but is generally 1 to 40% by weight, preferably 10 to 30% by weight. When a saccharide is used as an auxiliary, especially in the case where it is combined with the above cellulose ether derivative, desired effects can be obtained without incorporating a fat or oil or a wax, or a fatty acid, which is an auxiliary component.

When crystalline cellulose is used as a cellulosic polymer, a combination thereof with a polyacrylate ester derivative such as poly (methacrylic acid-co-ethyl acrylate), poly (methacrylic acid-co-methyl methacrylate) and poly (methyl methacrylate-co-ethyl acrylate), preferably Eudragid L30D-

5.5, and L100 (trade name; available from Lame Co., Germany) is recommended. The compounding amount of the polyacrylate ester derivative is generally 0.01 to 10% by weight, preferably 0.1 to 5% by weight.

As a carrier suitably usable in combination with CGRP or MAXs among later-described physiologically active substances, an ion complex comprising hyaluronic acid and a cationic polyacrylic acid derivative can also be mentioned. As to hyaluronic acid, any of those (straight-chain high molecular polysaccharides formed through alternate bonds derived from β-N-acetyl-D-glucosamine and β-D-glucuronic acid) derived from wide natural origins, for example, the connective tissues of mammals, cockscombs of chickens, capsules of streptococci, etc. can also be used. Suitable cationic polyacrylic acid derivatives such as poly (methyl methacrylate-co-butyl methacrylate-co-dimethylamino-ethyl methacrylate) and poly (ethyl acrylate-co-methyl methacrylate-co-trimethyl-aminonium ethyl methacrylate hydrochloride) include, for example, Eudragid E and Eudragid ES (trade names; available from Lame Co., Germany). As to the rate of mixing of them, they are suitably used almost in equal amounts.

Various physiologically active substances can be used, without particular limitation about kinds and action patterns contemplated thereon, so long as they can be prepared as a pharmaceutical preparation of the invention and can attain significant effects through continuous release. Such physiologically active substances include, for example, adrenaline, abscisic acid, arginine vasotocin, angiotensinogen, angiotensin, angiotensin I converting enzyme, succus gastricus-inhibiting polypeptides, insulin, insulin-like growth factors, S factor, erythropoietin, luteinizing hormone, luteinizing hormone-releasing hormone, progestogen, oxytocin, 2-octyl-γ-bromoacetoacetate, autacoids, gastrin, gastrin secretion-accelerating peptide, gastron, activated vitamin $D_3$, kallidin, calcitonin, calcitonin gene-related peptide (CGRP), kininogen, thymus hormone, glucagon, glucocorticoids, vasoactive small intestinal peptide, plasma kallikrein, serum factor, blood glucose-elevating hormone, thyroid-stimulating hormone, thyrotropin-releasing hormone, thyroid hormone, melanosite-stimulating hormone, melanosite-stimulating hormone-releasing hormone, melanosite-stimulating hormone release-inhibiting hormone, corticotropin-like middle lobe peptide, urokinase, chole-cystokinin octapeptide, cholecystokinin tetrapeptide, cholecystokinin variant, cholecystokinin-12, cholecystokinin pancreothymine, cholecystokinin, growth factor, substance P, female sex hormones, adipokinin, chorionic gonadotropin, nerve growth factor, pancreatic polypeptides, reproduction nest-stimulating substance, gonadotropic hormones, growth hormone, growth hormone-releasing factor, secretin, caerulein, serotonin, fibroblast growth factor, kallikrein glandularis, somatostatin, somatomedins A and B, placental lactogen, thymosin, thymopoietin, thyroglobulin, traumatic acid, endothelial cell growth factor, mollusc heart stimulant nervous peptide, neurotensin, equine serum gonadotropic hormone, brain hormones, noradrenaline, vasopressin, estrogenic hormone, histamine, epidermic cell growth factor, parathyroid hormone, parathyroid-stimulating hormone, corticotropin-releasing factor, adrenal cortical hormone, PACAP, bradykinin, bradykinin-like peptide, proinsulin, proopiomelano-cortin, prostaglanadins, pro PTH, prolactin, prolactin-releasing hormone, prolactin release-inhibiting hormone, florigene, human menopausal gonadotropin, bombesine, maxadilans (MAXs), mineral corticoid, light-adapted horomone, methionyllysylbradykinin, 1-methyladrenine, melatonin, motilin, androgen, diuretic hormone, lipotropin, renin, relaxin and follicle maturation hormone.

Among physiologically active substances including those enumerated above, those usable for prophylaxis or treatment of cerebral vasospasm, which is a preferred embodiment of the invention, specifically include CGRP, MAXs, deferoxamine, methylprednisolone, nieorandil, nicaraben, magnesium sulfate, aetinomyein D, 21-amino-steroid, isoproterenol, tPA, nimodipine, hydroeortisone, nicardipine, nifedipine, diltiazem, dilazp, teprothid, AA861, papaverine, OKY 1581, amyl nitrite, erythrityl tetranitrate, isosorbide dinitrate, nitroglycerin, pentaerythritol tetronitrate, VIP, vasopressin, bradykinin, PACAP, SOD, catalase, bepridil, nadololol, felodipine, isradipine, varapamil, atenolol, metoprolol and propanolol.

Among them, compounds having a vasodilative action, particularly CGRP and MAXs can be mentioned as those which exert significant effects, particularly in prophylaxis or treatment of cerebral vasospasm, in combination with carriers in accordance with the invention of the present application, or in combination with other carriers capable of continuously releasing physiologically active substances, specifically by intracorporeal implantation, particularly by intrathecal implantation.

The abbreviation of MAXs is used herein in a conception of including a natural-occurring peptide (or protein) (SEQ ID NO: 1) derived from the sand fly Lutzomyia longipalpis disclosed in above-mentioned E. A. Lerner et al., WO 91/00293 and its recombinant peptides; and the GIL-modified maxadilan (see, SEQ ID NO: 2; E. A. Lerner et al., J. Bio. Chem., Vol. 267 (2), pp. 1062–1066, 1992) wherein its N-terminus is modified with a sequence consisting of three amino acid residues, GIL-; and their analogues. A representative analogue includes a peptide fragment obtained, according to the method disclosed in E. A. Lerner et al., ibid., namely by obtaining a particular modified-type maxadilan-fused protein, and then disgesting it with a protease such as factor Xa or thrombin. Representative among them are a peptide (SEQ ID NO: 3) wherein an amino acid sequence residue GSIL- is bonded to the N-terminus of SEQ ID NO: 1 maxadilan, and a peptide (SEQ ID NO: 4) wherein an amino acid sequence residue LVPRGSIL- is bonded thereto. MAXs also include those wherein one or more amino acid residues in the amino acid sequence are deleted or replaced, and those wherein one or more amino acid residues are added to the N-terminus or C-terminus, and may be converted amino acid residues—Lys Ala Gly Lys at the C-terminus thereof to—Lys Ala-$NH_2$.

A person skilled in the art will be able to obtain MAXs usable in the invention, referring to the amino acid sequences specifically disclosed in SEQ ID NOs.: 1 to 4 of the above Sequence Listing, by a liquid phase or solid phase peptide synthesis method known per se, or by a recombinant method wherein a nucleotide sequence is used which encodes a sequence formed by deleting one or more amino acid residues in its amino acid sequence or their amino acid sequences, or replacing them by other amino acid residue(s), or adding other amino acid residue(s) into the sequence(s).

The level of a physiologically active substance which can be contained in the pharmaceutical preparations of the invention composed of the above-mentioned carriers and optionally used auxiliaries is not limited since the optimal amount varies depending on kinds of carriers and active substances to be used, and methods for application of the preparations. However, generally, it is possible to incorporate $1\times10^{-12}$ to 30% by weight, preferably $1\times10^{-4}$ to 5% by weight of a physiologically active substance, based on the total weight of the pharmaceutical preparation, into the preparation.

The pharmaceutical preparations of the invention can be prepared by compounding the above-mentioned carrier-constituting components and physiologically active substances at levels described above, respectively, and using formulation techniques known per se. In such formulation, it is possible to incorporate one or more of optional additives conventionally used in the art, for example, disintegration-adjusting agents, stabilizers, antioxidants, wetting agents, binders, lubricants, etc., in accordance with the forms of use of the pharmaceutical preparations. The dosage forms of preparations thus prepared can usually be tablets, pills or capsules. However, the dosage form of the preparations may also be a liquid obtained by pulverizing a solid agent prepared above so that it can be used as an injection, and suspending the powder in a suitable fluid (e.g., sterilized distilled water, physiological saline, etc.).

On the other hand, it is known that part of MAXs among the above physiologically active substances have a vasodilative action, as is the case with CGRP, as disclosed by the above E. A. Lerner et al. For example, the maxadilan of SEQ ID NO: 2 exhibits an extremely interesting vasodilative action 80 to 100 times higher than that of CGRP. An N-terminus-modified-type maxadilan denoted by SEQ ID NO: 3 is known to exhibit a vasodilative action (particularly, erythema activities) further about 10 times higher than that of SEQ ID NO: 2 (the above M. Ohnuma et al., Peptide Chemistry 1993: Y. Okada (Ed.), pp. 145–148), and is a particularly interesting peptide.

However, it has not so far been disclosed in technical literatures that these MAXs can be used for prophylaxis or treatment of cerebral vasospasm.

Thus, according to this invention, although cerebral vasospasm can be prevented or treated by implanting a pharmaceutical preparation comprising the above carriers having contained therein at least one of MAXs, preferably into a living body, particularly into the brain, a method to use MAXs for treating the disease without using these carriers is also disclosed.

Namely, this invention also provides a method for prophylaxis or treatment of cerebral vasospasm which comprises a step of administering an effective amount of at least one of MAXs into the body of a patient to whom cerebral vasospasm may occur or a patient to whom cerebral vasospasm occurred. This administration step can, for example, be performed by administering an injection obtained by merely dissolving or suspending at least one of MAXs in sterilized distilled water, physiological saline or a buffered solution, into the vein or artery, or can also be performed by administering preparations obtained by adding various inorganic salts as an ionic strength-adjusting agent, and other excipients, for example, dextrin, lactose, starch, etc. thereto, and formulating the mixtures.

Administration time varies depending on dosage forms adopted, administration routes, and the purpose of use (prophylaxis or treatment), but can usually be immediately to 10 days after the operation of subarachnoid hemorrhage.

Thus, this invention also provides as another embodiment the use of at least one of MAXs for preparing a pharmaceutical preparation for prophylaxis or treatment of cerebral vasospasm. The use of prolonged releasing pharmaceutical preparations of CGRP or MAXs for intrathecal implantation has not so far been disclosed in technical literatures, either, and, in addition, has a significantly excellent advantage, for example, over administration of a sterile aqueous solution of CGRP into the cisterna magna, as disclosed in the above H. Shimizu et al., No Shinkei Geka, 22(2):131–139, 1994.

A further important thing is that effective prophylaxis or treatment of cerebral vasospasm can be performed not only by combinations of the above-mentioned carriers for pharmaceutical preparations with CGRP or MAXs, but also by implanting into the brains pharmaceutical preparations prepared by combinations of physiologically active substances exhibiting a vasodilative action, as mentioned above with other carriers.

Thus, from this viewpoint, as stated above, this invention also provides a method for prophylaxis or treatment of cerebral vasospasm which comprises a step of implanting a prolonged releasing pharmaceutical preparation comprising certain carriers having contained therein a physiologically active substance having a vasodilative action, preferably at least one selected from the group consisting of CGRP and MAXs, into the brain of a patient to whom cerebral vasospasm may occur or a patient to whom cerebral vasospasm occurred. As an alternative embodiment of this method, this invention also provides the use of a physiologically active substance (or compound) having a vasodilative action, preferably at least one selected from the group consisting of CGRP and MAXs, for preparing an intrathecal implantation-type pharmaceutical preparation for prophylaxis or treatment of cerebral vasospasm.

The pharmaceutical preparation of the invention of the present application can be administered in a predetermined effective amount in a prolonged releasable form, particularly parenterally, but preferably, the characteristic of the preparation lies in a point that it exhibits a remarkable effect when implanted into a living body, particularly into the brain. The pharmaceutical preparation of the invention, when thus implanted into the brain, prolonged releases the active substance with retention of the dosage form for 7 days or more, mostly 10 days or more, and thus the active substance distributes only on the administration site and does not disperse throughout the brain. Therefore, there is not waste of the active substance, and moreover, there is less possibility that it has unnecessary actions on other sites. Moreover, the preparation has desired properties that it does not hurt the cells at the administration site, and releases that active substance stably over a long term as long as 2 days to 2 weeks after the administration, and thereafter the base (carriers and auxiliaries) is absorbed in the living body. When the preparation is intrathecally implanted as a tablet, it is desirable to place it in the subarachnoid space and/or in the furrow of the brain surface so that it is not let to flow by the reflux of the cerebrospinal fluids. It is also desirable that the thickness of the preparation is 5 mm or less so that it can be intrathecally implanted without any trouble, and since when the expansion coefficient of the tablet is too large, it may do damages such as cell detachment to the cells and/or tissues around the administration site, and therefore, it is desirable to adjust the carrier components and the auxiliary components to make the expansion coefficient 200% or less.

A person skilled in the art will be able to readily determine the optimal amounts of physiologically active substances which can be incorporated in these prolonged releasing pharmaceutical preparations, according to in vitro tests or in vivo tests as described later.

This invention is further illustrated below according to specific examples, but it should not be construed that they are provided for the purpose of limiting the scope of the invention.

Example 1

Preparation of a prolonged releasing pharmaceutical preparation (P-I)

10 g of stearic acid and 19 g of hardened oil were mixed, 2.0 g of 0.4% CGRP solution (corresponding to 8 mg of CGRP) and 20 g of lactose were added thereto and the mixture was mixed, and 60 g of hydroxypropyl-cellulose was added thereto. The mixture was mixed adequately, and then subjected to a KBr compressor (150 kg, 1 minute) to prepare tabular tablets (P-I) having a diameter of 13 mm.

Example 2

Preparation of a prolonged releasing pharmaceutical preparation (P-II)

20 g of stearic acid and 20 g of hardened oil were mixed, 2.5 g of 0.4% CGRP solution (corresponding to 10 mg of CGRP) and 20 g of lactose were added thereto and the mixture was mixed, and 40 g of hydroxypropyl-cellulose was added thereto. The mixture was mixed adequately, and then pressure molded using a Correct 19K compressor (KIKUSUI CLEAN PRESS) (6 mm$\phi$×2 mm).

Example 3

Preparation of a prolonged releasing pharmaceutical preparation (P-III)

15 g of palmitic acid and 15 g of beeswax were mixed, 2.0 g of 0.4% CGRP solution (corresponding to 8 mg of CGRP) was added thereto and the mixture was mixed, and 70 g of hydroxypropylcellulose was added thereto. The mixture was mixed adequately, and then pressure molded using a Correct 19K compressor (KIKUSUI CLEAN PRESS) (6 mm$\phi$×2 mm).

Example 4

Preparation of a prolonged releasing pharmaceutical preparation (P-IV)

10 g of stearic acid and 10 g of hardened oil were mixed, 2.0 g of 0.4% CGRP solution (corresponding to 8 mg of CGRP) and 20 g of glucose were added thereto and the mixture was mixed, and 60 g of hydroxypropyl-cellulose was added thereto. The mixture was mixed adequately, and then pressure molded using a Correct 19K compressor (KIKUSUI CLEAN PRESS) (6 mm$\phi$×2 mm).

Example 5

Preparation of a prolonged releasing pharmaceutical preparation (P-V)

10 g of stearic acid and 10 g of hardened oil were mixed, 2.5 g of 1.6% CGRP solution (corresponding to 40 mg of CGRP) and 20 g of lactose were added thereto and the mixture was mixed, and 60 g of hydroxypropyl-cellulose was added thereto. The mixture was mixed adequately, and then pressure molded using a Correct 19K compressor (KIKUSUI CLEAN PRESS) (6 mm$\phi$×2 mm).

Example 6

Preparation of a prolonged releasing pharmaceutical preparation (P-VI)

10 g of stearic acid and 10 g of hardened oil were mixed, 2.5 g of 10% CGRP solution (corresponding to 250 mg of CGRP) and 20 g of lactose were added thereto and the mixture was mixed, and 60 g of hydroxypropyl-cellulose was added thereto. The mixture was mixed adequately, and then pressure molded using a Correct 19K compressor (KIKUSUI CLEAN PRESS) (6 mm$\phi$×2 mm).

Example 7

Preparation of a prolonged releasing pharmaceutical preparation (P-VII)

10 g of stearic acid and 10 g of hardened oil were mixed, 2.5 g of 0.6% solution of a GSIL-modified-type maxadilan denoted by SEQ ID NO: 3 (corresponding to 15 mg of SEQ ID NO: 3) and 20 g of lactose were added thereto and the mixture was mixed, and 60 g of hydroxy-propylcellulose was added thereto. The mixture was mixed adequately, and then pressure molded using a Correct 19K compressor (KIKUSUI CLEAN PRESS), and the moldings were pulverized and mixed and pressure molded again using the same compressor (6 mm$\phi$×2 mm).

Example 8

Preparation of a prolonged releasing pharmaceutical preparation (P-VIII)

10 g of stearic acid and 10 g of hardened oil were mixed, 2.5 g of 1.0% solution of a GSIL-modified-type maxadilan denoted by SEQ ID NO: 3 (corresponding to 25 mg of SEQ ID NO: 3) and 20 g of lactose were added thereto and the mixture was mixed, and 60 g of hydroxy-propylcellulose was added thereto. The mixture was mixed adequately, and then pressure molded using a Correct 19K compressor (KIKUSUI CLEAN PRESS), and the moldings were pulverized and mixed and pressure molded again using the same compressor (6 mm$\phi$×2 mm).

Example 9

Preparation of a prolonged releasing pharmaceutical preparation (P-IX)

10 g of stearic acid and 10 g of hardened oil were mixed, 2.5 g of 10% solution of a GSIL-modified-type maxadilan denoted by SEQ ID NO: 3 (corresponding to 250 mg of SEQ ID NO: 3) and 20 g of lactose were added thereto and the mixture was mixed, and 60 g of hydroxy-propylcellulose was added thereto. The mixture was mixed adequately, and then pressure molded using a Correct 19K compressor (KIKUSUI CLEAN PRESS), and the moldings were pulverized and mixed and pressure molded again using the same compressor (6 mm$\phi$×2 mm).

Example 10

Preparation of a prolonged releasing pharmaceutical preparation (P-X)

15 g of palmitic acid and 15 g of beeswax were mixed, 3.0 g of 0.4% solution of a GSIL-modified-type maxadilan denoted by SEQ ID NO: 3 (corresponding to 10 mg of SEQ ID NO: 3) was added thereto and the mixture was mixed, and 70 g of hydroxypropylcellulose was added thereto. The mixture was mixed adequately, and then pressure molded using a Correct 19K compressor (KIKUSUI CLEAN PRESS) (6 mm$\phi$×2 mm).

Example 11

Preparation of a prolonged releasing pharmaceutical preparation (P-XI)

2.0 g of 0.4% CGRP solution (corresponding to 8 mg of CGRP) and 20 g of lactose were mixed adequately, and 80 g of hydroxypropylcellulose was added thereto. The mixture was mixed adequately, and then subjected to a KBr compressor (150 kg, 1 minute) to prepare tabular tablets (P-XI) having a diameter of 13 mm.

Example 12

Preparation of a prolonged releasing pharmaceutical preparation (P-XII)

2.5 g of 0.4% CGRP solution (corresponding to 10 mg of CGRP) and 20 g of glucose were mixed adequately, and 80 g of methylcellulose was added thereto. The mixture was mixed adequately, and then subjected to a KBr compressor (150 kg, 1 minute) to prepare tabular tablets (P-XII) having a diameter of 13 mm.

Example 13

Preparation of a prolonged releasing pharmaceutical preparation (P-XIII)

2.5 g of 0.4% CGRP solution (corresponding to 10 mg of CGRP) and 13 g of poly (methacrylic acid-co-methyl methacrylate), Eudragid L-100 (trade name; available from Lame Co., Germany), were mixed, and 87 g of crystalline cellulose was added thereto. The mixture was mixed adequately, and then subjected to a KBr compressor (150 kg, 1 minute) to prepare tablets (P-XIII) having a diameter of 13 mm.

Example 14

Preparation of a prolonged releasing pharmaceutical preparation (P-XIV)

17 g of stearic acid and 17 g of hydrogenated oil (hydrogenated castor oil) were mixed, 2.0 g of 0.4% CGRP solution (corresponding to 8 mg of CGRP) and 0.3 g of poly (methacrylic acid-co-ethyl acrylate), of Eudragid L30D-5.5 (trade name; available from Lame Co., Germany), were added and the mixture was mixed, and 66 g of crystalline cellulose was added thereto. The mixture was mixed adequately, and then subjected to a KBr compressor (150 fkg/cm$^2$, 1 minute) to prepare tablets (P-XIV) having a diameter of 13 mm.

Example 15

Preparation of a prolonged releasing pharmaceutical preparation (P-XV)

100 g of aqueous 2% hyaluronic acid solution and 100 g of aqueous 2% Eudragid E solution were subjected to reaction at room temperature for 2 hours under stirring. The reaction mixture was centrifuged at 3,000 rpm for 10 minutes, and the product was recovered and vacuum dried to give a polyion complex of hyaluronic acid Eudragid E.

The obtained solid was pulverized and classified to give powder having a particle size of 150 microns or less. 100 g of the powder and 0.75 of 0.4% CGRP solution (corresponding to 3 mg of CGRP) were mixed, and then pressure molded using a Correct 19K compressor (KIKUSUI CLEAN PRESS), and the moldings were pulverized and mixed and pressure molded again using the same compressor (6 mm$\phi$×2 mm).

Examples 16 to 20

Procedures described in the aforementioned Examples, particularly Examples 14 and 15, are repeated, except that compositions of the preparation are those used in the following table 1.

TABLE 1

| Compositions | Example Nos. (preparation Nos.) | | | | |
|---|---|---|---|---|---|
| | 16 (P-XVI) | 17 (P-XVII) | 18 (P-XVIII) | 19 (P-XIX) | 20 (P-XX) |
| Crystalline cellulose (mg) | 1600 | 1450 | 1300 | 2000 | 0 |
| Hydrogenated oil (hydrogenated caster oil) (mg) | 200 | 270 | 330 | 0 | 0 |
| Stearic acid (mg) | 200 | 270 | 330 | 0 | 0 |
| Eudragit ® L30D-5.5 (μl) | 120 | 110 | 100 | 300 | 300 |
| Eudragit ® L100 (g) | 0 | 0 | 0 | 0.4 | 0.2 |
| CMC · Na (g) | 0 | 0 | 0 | 0 | 1.5 |
| Lactose (g) | 0 | 0 | 0 | 0 | 0.5 |
| CGRP (mg) | 0.2 | 0.2 | 0.2 | 0.2 | 0.2 |
| H$_2$O (ml) | 0.2 | 0.2 | 0.2 | 0.2 | 0.2 |
| Ethanol (ml) | 0 | 0 | 0 | 5 | 0 |

Examples 21 to 34

In vitro release test on physiologically active substances 5 ml portions of Hartmann's Solution (available from The Green Cross Corp., Japan) were aseptically put in 15-ml tubes, respectively.

Figure 2:
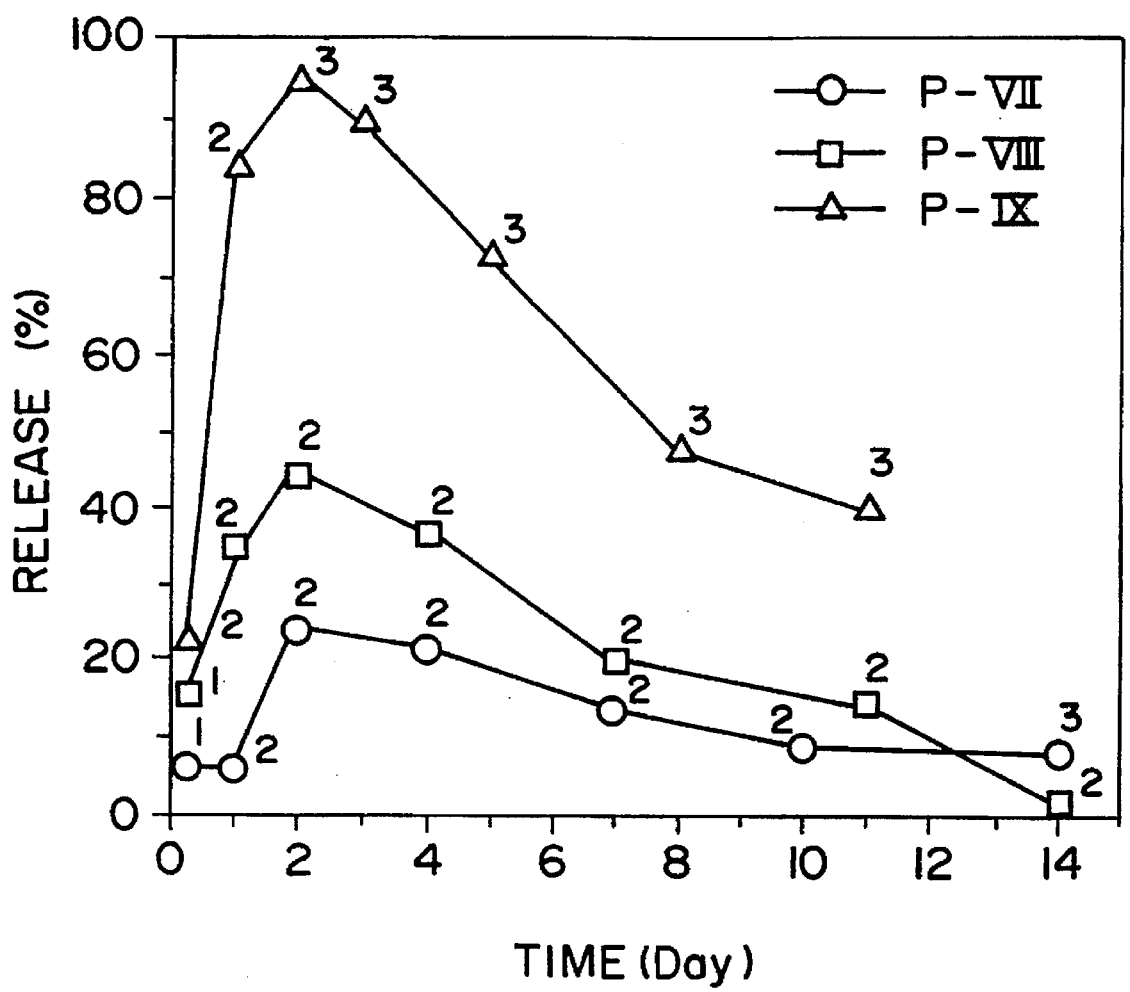
FIG. 2 is a graph showing the behaviors of release of maxadilan (SEQ ID NO: 3) from pharmaceutical Preparations of the invention, P-VII, P-VIII and P-IX (prepared in Example 7, Example 8 and Example 9, respectively) in the in vitro test.
Figure 3:
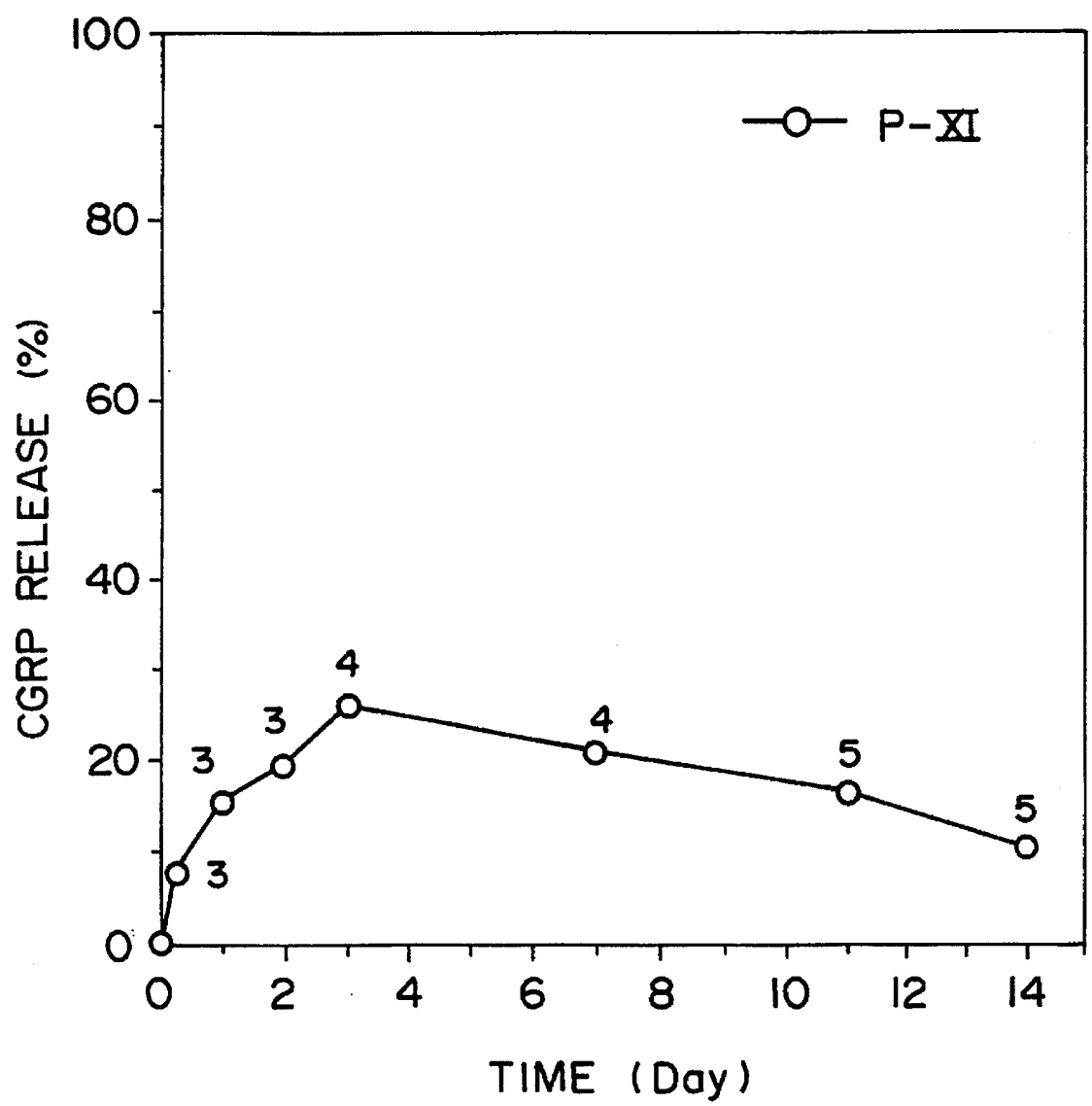
FIG. 3 is a graph showing the behavior of release of CGRP from a Pharmaceutical Preparation of the invention, P-XI (prepared in Example 11)
Figure 4:
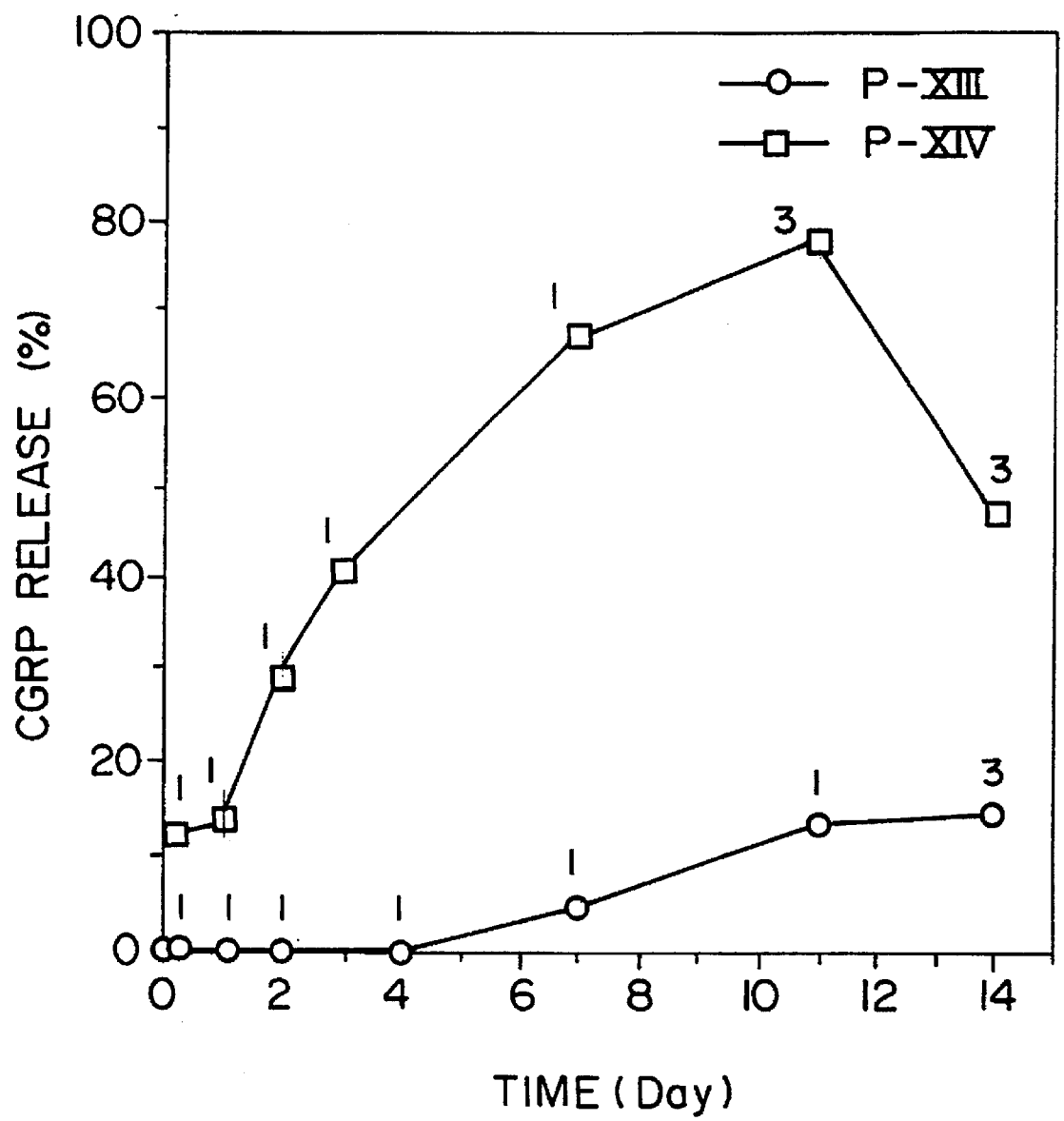
FIG. 4 is a graph showing the behaviors of release of CGRP from Pharmaceutical Preparations of the invention, P-XIII and P-XIV (prepared in Example 13 and Example 14, respectively) in the in vitro test.
Figure 5:
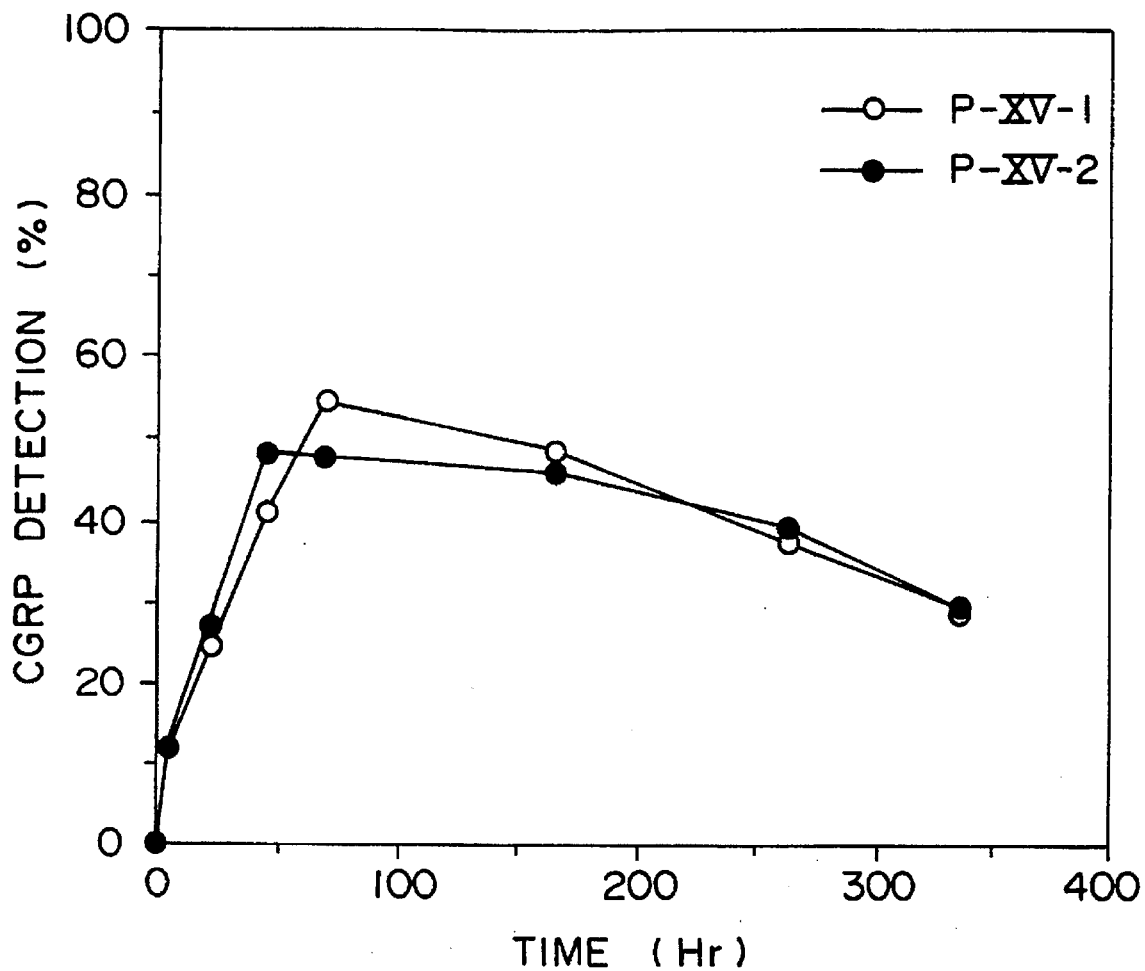
FIGS. 5, and 6 to 8 are a graph showing the behaviors of release of CGRP from pharmaceutical preparations of the invention, P-XV-1 and P-XV-2 (both prepared in Example 15), and P-XVI to P-XX (prepared in Examples 16 to 20), in the in Mitro test.
Figure 6:
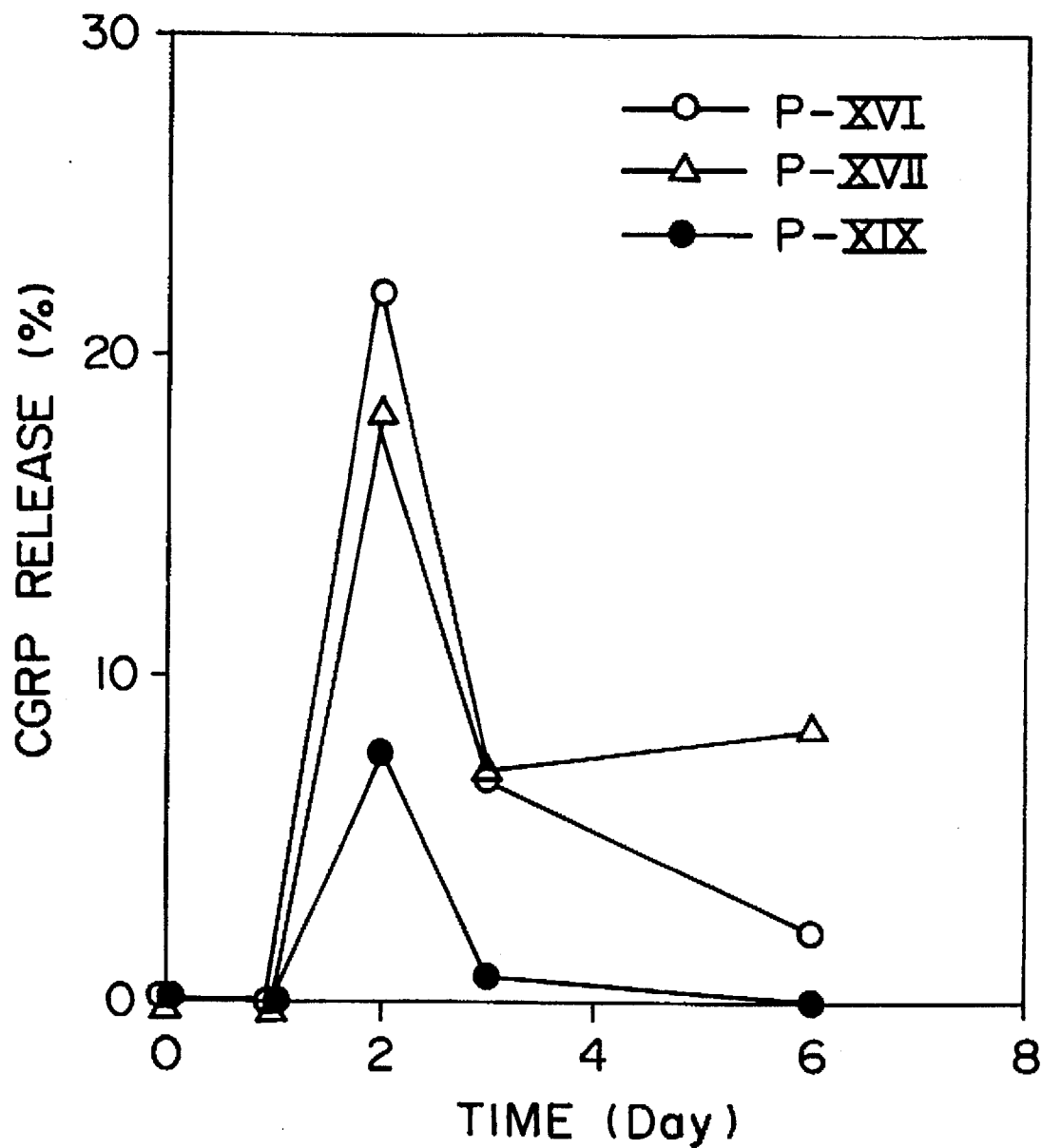
Figure 7:
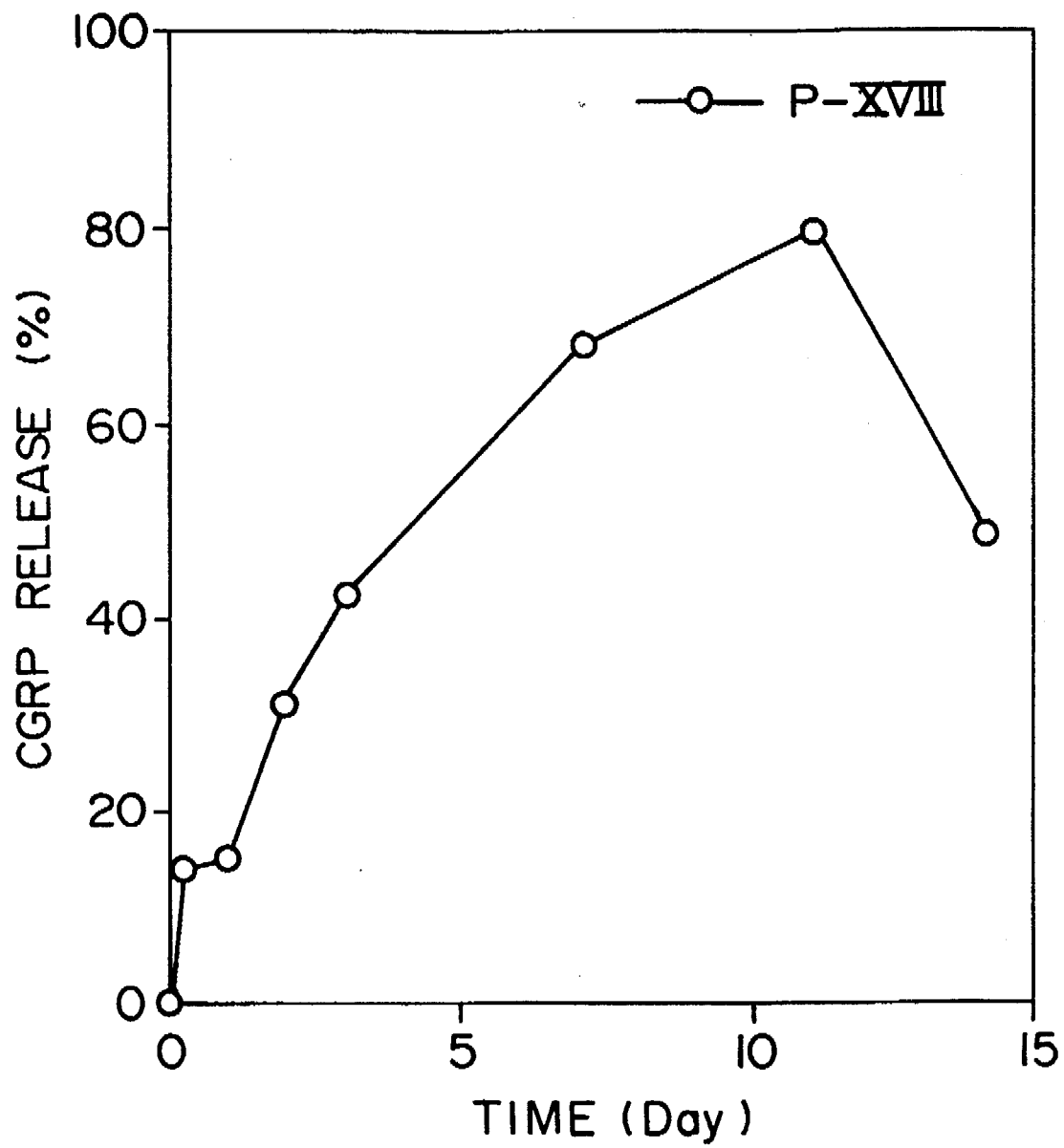
Figure 8:
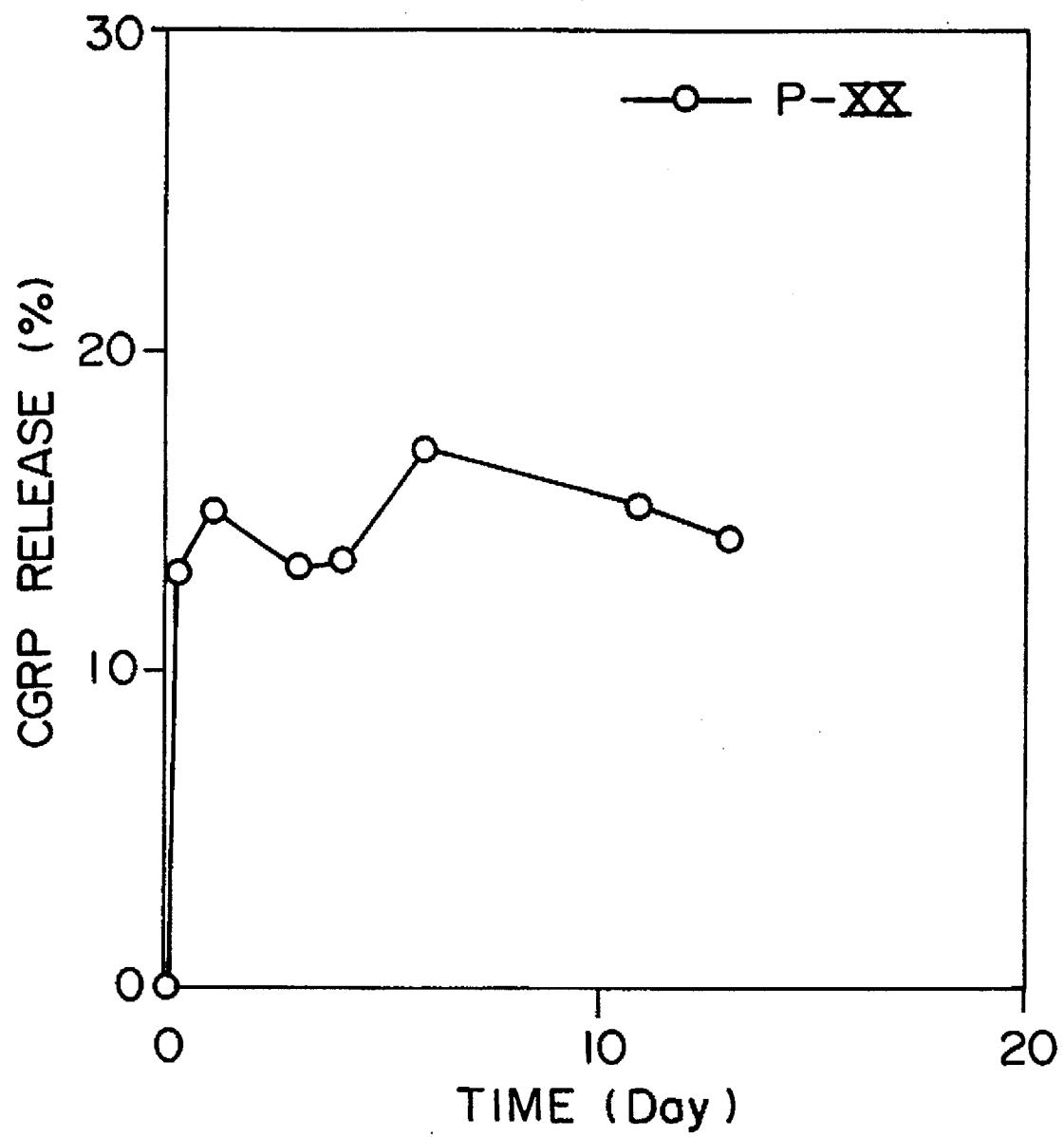

The following pharmaceutical preparations were aseptically put in these tubes, respectively:

P-I, P-II, P-IV (FIG. 1)
P-VII, P-VIII, P-IX (FIG. 2)
P-XI (FIG. 3)
P-XIII, P-XIV (FIG. 4)
P-XV (FIG. 5)
P-XVI, P-XVII, P-XIX (FIG. 6)
P-XVIII (FIG. 7)
P-XX (FIG. 8)

The mixtures were shaken at 37° C. and 120 rpm, sampling was performed 1, 2, 3, 7, 11 and 14 days thereafter, and each sample was subjected to determination of the release amount of the physiologically active substance by high performance liquid chromatography. The results are shown in FIGS. 1 to 8, respectively (The relations between the figures and the pharmaceutical preparations are shown in the above parentheses).

Numbers in the figures express the disintegration states of the tablets, and the meanings are as follows:

Disintegration state
1:No change
2: 20 % swelling is observed
3:Small cracks are formed 4:Large cracks are formed 5:Disintegrated into pieces

Example 35

In vivo release test on a physiologically active substance

Figure 9:
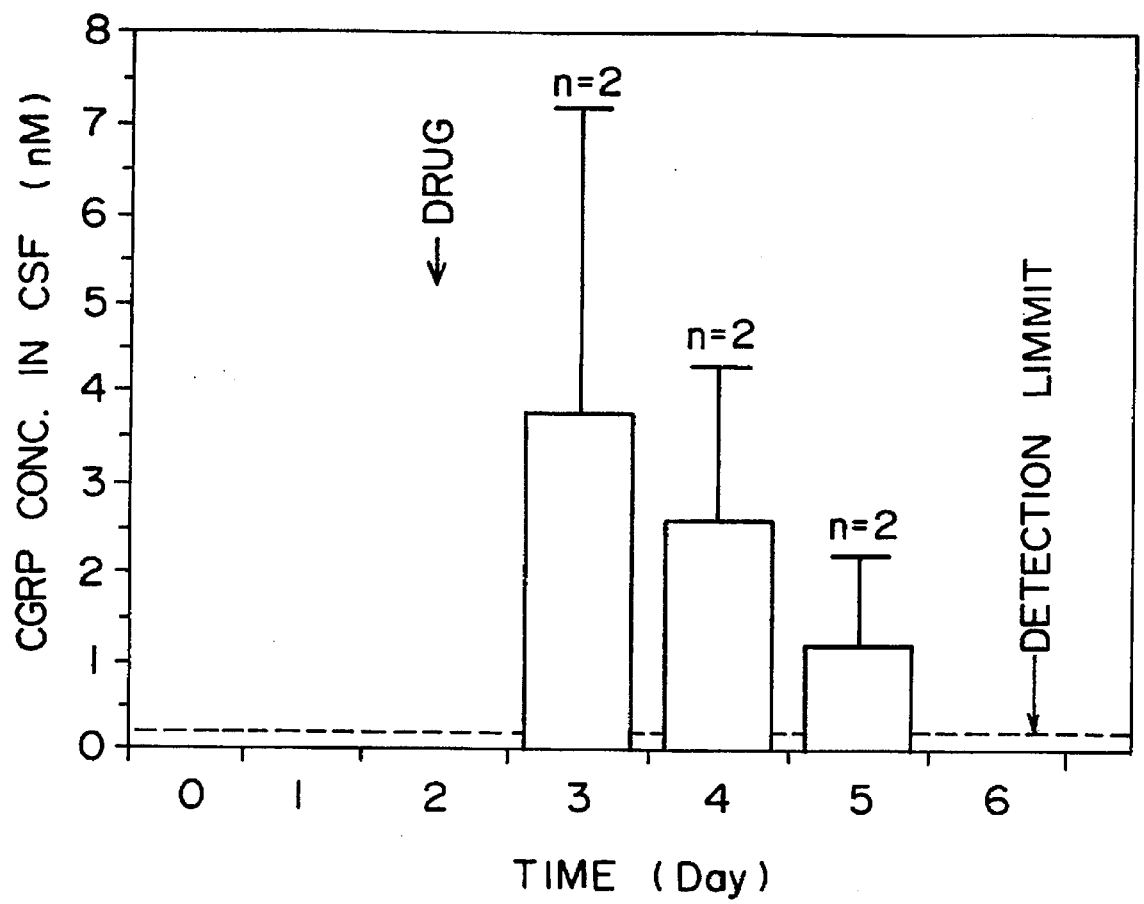
FIG. 9 is a graph showing the behavior of release of CGRP from a Pharmaceutical Preparation of the invention, P-II, implanted into the brain of a rabbit.

An in vivo test on drug release effect with 3 rabbits according to the method shown below was performed, using the tablets (P-II) obtained in Example 2. The results are shown in FIG. 9.

Test method

Method of intrathecally implantation of the tablets into the brains

The rabbits (2.5–3.0 kg) after sodium pentobarbital anesthesia were fixed on their faces, the occipital bone membranes (dura maters) were exposed by incision, and the occipital bones were shaved by a drill to expose the dura maters further wider. Thereafter, the dura maters and the arachnoidmembrane were incised to a length of about 8 mm, the tablets of the prolonged releasing pharmaceutical preparation of Example 2 were implanted there on two of the three animals, a placebo tablet was implanted there on the other one, the dura maters, the muscles and the skins were sutured, and an appropriate amount of an antibiotic was administered to the incision sites, respectively.

The cerebrospinal fluids were sampled every day from the rabbits by the following sampling method, respectively, and the samples were assayed for the CGRP concentrations (nM) in the cerebrospinal fluids according to the following assay method.

Method of sampling of the cerebrospinal fluids

The rabbits after sodium pentobarbital anesthesia were fixed on their faces, the occipital bone membranes (dura maters) were exposed by incision, the occipital bone membranes were incised, and the celebrospinal fluids were sampled therefrom.

Method of assay of the concentration of the physiologically active substance in the celebrospinal fluids The concentrations were assayed by the following radioimmunoassay.

4,000 cpm portions of a labeling compound [2-($^{125}$I-iodohistidyl$^{10}$)CGRP] were put in measuring tubes, and separately from these, 100 µl portions of 1, 2, 5, 10, 50, 100, 500 and 100 fmol standard solutions were prepared using synthesized CGRP (available from Bachem Co.). 100 µl portions of an antibody (obtained by dissolving RPN 1841 available from Amarsham Co. in 2 ml and diluting the solution to 12.5 ml) and 600 µl portions of an analyzing buffer [50 mM sodium phosphate (pH 7.4), 0.3% bovine serum albumin, 10 mM EDTA] were added, respectively, to the tubes containing 100 µl portions of the test samples, the standard solutions or water, respectively, the covers of the tubes were shut, and the mixtures were allowed to stand at 4° C. for 5 days, 250 µl of a dextran/active carbon solution [50 mM sodium phosphate (pH 7.4), 0.25% gelatin, 10 mM EDTA] was added to each mixture, and the resultant mixture was immediately centrifuged at 2,000×g for 20 minutes. Both of the precipitate and the supernatant were measured for 200 seconds by a γ-counter, and the concentration of the physiologically active substance (CGRP) in the cerebrospinal fluid was assayed based on the standard curve obtained from the standard substance solutions.

Separately, an in vivo test related to the disintegration state of a tablet was performed using the tablet of P-II as the tablet and a rabbit other than the above rabbits. In this connection, implantation of the tablet into the brain was performed in the same manner as above, and the disintegration state of the tablet was observed through craniotomy. The results are shown below. The following numerical values exhibit the disintegration state of the tablet, and the meanings are the same as defined above.

| After implantation | 1st day | 5th day | 10th day |
| --- | --- | --- | --- |
| Disintegration state | 2 | 2 | 4 |

It is understood from the results that the prolonged releasing cerebral vasospasm inhibitor of the invention keeps the dosage from in vivo even 10 days after the intrathecal implantation.

Examples 36 and 37

Vasodilative test (I)

Figure 10:
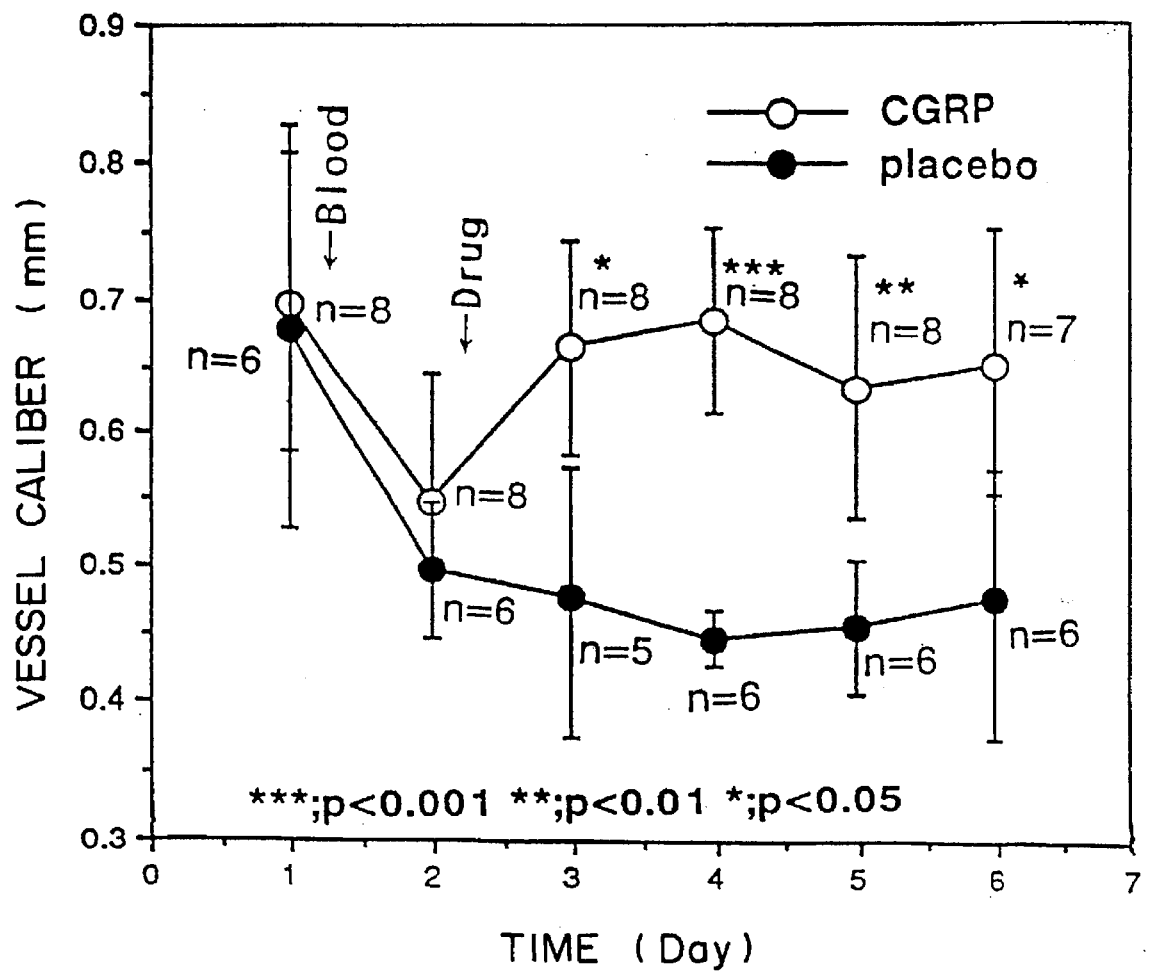
FIGS. 10 and 11 show results obtained by implanting preparations of the invention, P-V and P-VI, into the brain, particularly at the subarachnoid region of model animals of subarachnoid hemorrhage, respectively, and observing the behaviors of vasodilative.
Figure 11:
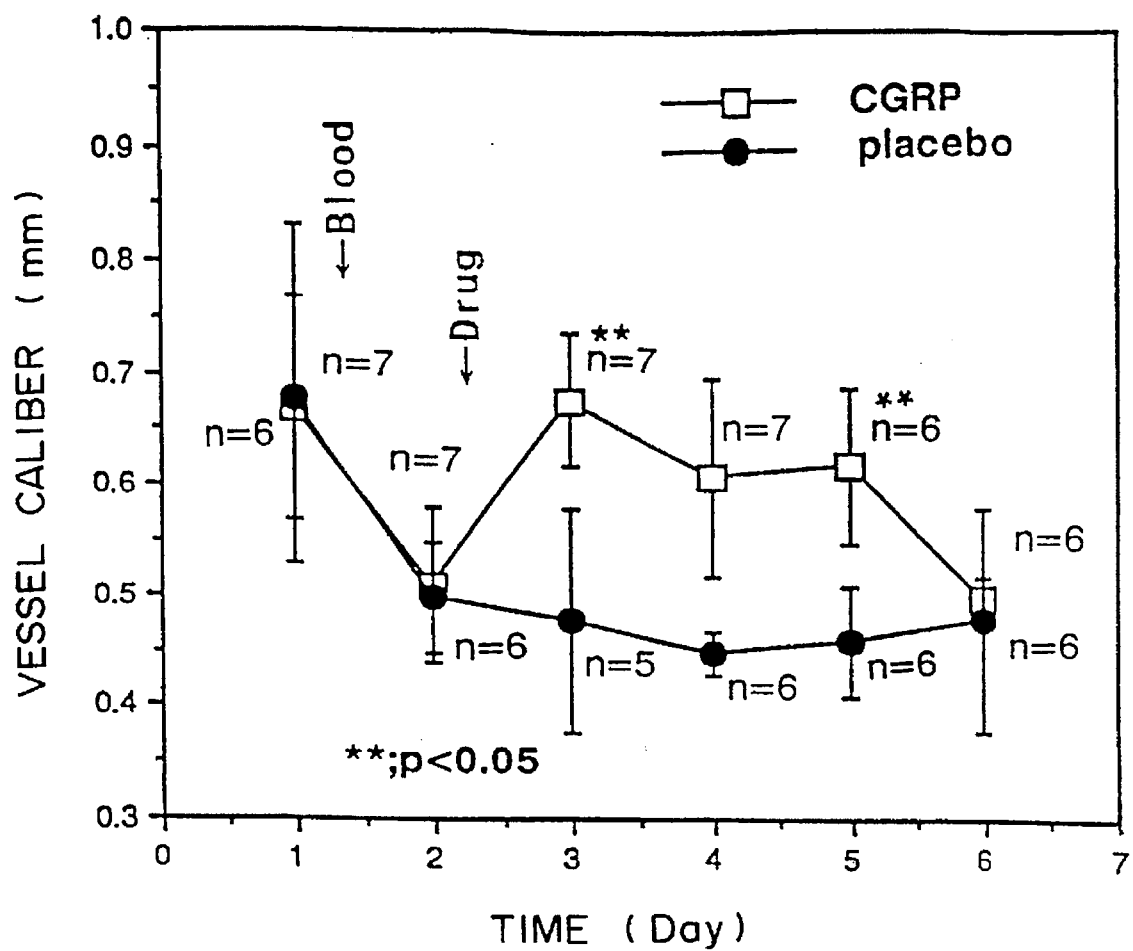

A vasodilative test was performed according the following method, using the tablets obtained in Example 5 and Example 6, i.e. P-V and P-VI, respectively, and tablets not containing a physiologically active peptide CGRP (placebo tablets). The results are shown in FIG. 10 about the tablet of P-V and in FIG. 11 about the tablet of P-VI.

Process of preparation of the placebo tablet

Prolonged releasing pharmaceutical preparations as placebos were prepared in the same manners as in the preparation of the prolonged releasing pharmaceutical preparation of Example 5 (P-V) and in the preparation of the prolonged releasing pharmaceutical preparation of Example 6 (P-VI), respectively, except for replacement of CGRP by hydroxypropylcellulose.

Vasodilative test

An experiment was performed according to the following procedure using 8 rabbits about the tablet of P-V and 7 rabbits about the tablet of P-VI, these rabbits weighing 2.5 to 3 kg.

(1) After an X-ray photograph of the basilar artery of each rabbit was taken, subarachnoid hemorrhage models were prepared according to a known method [D. G. Vollmer et al., Neurosurgery 28:27–32 (1991)]. (Day 0)

(2) 24 hours later (Day 1), each animal was anesthetized with sodium pentobarbital, and the occipital region was incised from the occipital bone to the primary cervical vertebrae along the median line.

(3) The muscles attached to the occipital bone, the primary cervical vertebrae and the occipital bone membrane were carefully detached by a knife so as not to injure the vein.

(4) The exposed occipital bone was shaved by a surgical drill to a thickness of the order of 2 to 5 mm from the lower part.

(5) Thereafter, the occipital bone membrane was incised by a knife to a length of the order of 8 to 10 mm.

(6) The tablet was placed in the subarachnoid region through this site using a pair of tweezers.

(7) After the insertion of the tablet, the occipital bone membrane was sutured with silk thread.

(8) The cut portion was further shut with Aron Alpha (trade mark) along the suture line.

(9) Thereafter, the muscle and the skin were sutured with silk thread, and an appropriate amount of antibiotic was administered.

(10) The blood vessel calibers were measured every day from immediately after the administration to 5 days thereafter (Day 6) by angiography.

Comparative example

Comparative tests against Example 35 and Examples 36 and 37

Figure 12:
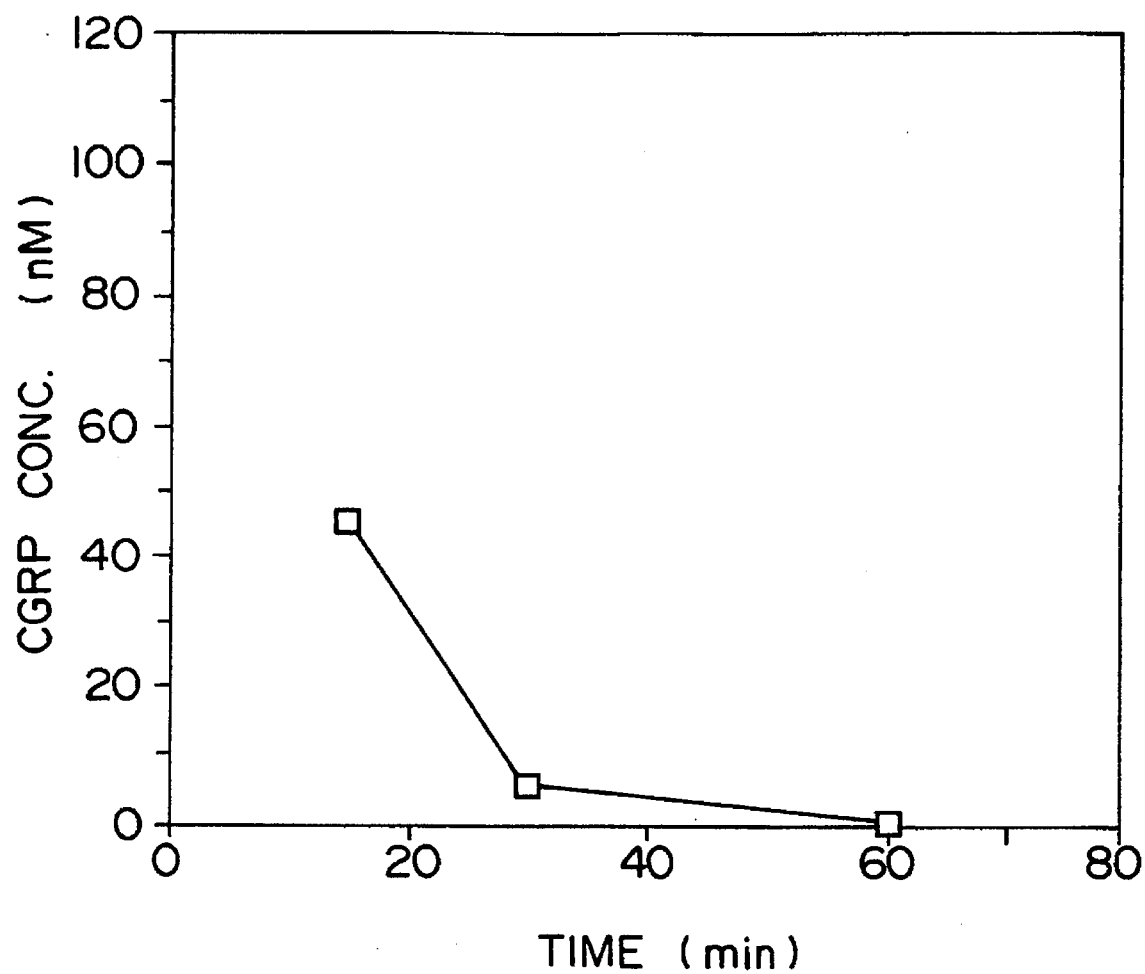
FIG. 12 is a graph showing change of the CGRP concentration in the CSF when an aqueous CGRP solution was administered to a rabbit by a cisternal puncture method, and showing stability of CGRP in the CSF.

As a comparative example, an aqueous CGRP solution was administered to one rabbit by a cisternal puncture method in accordance with the known method in the above (1), and the CGRP concentration (nM) in the cerebrospinal fluid was assayed over the lapse of time in the same manner as in Example 35. The results are shown in FIG. 12.

Figure 13:
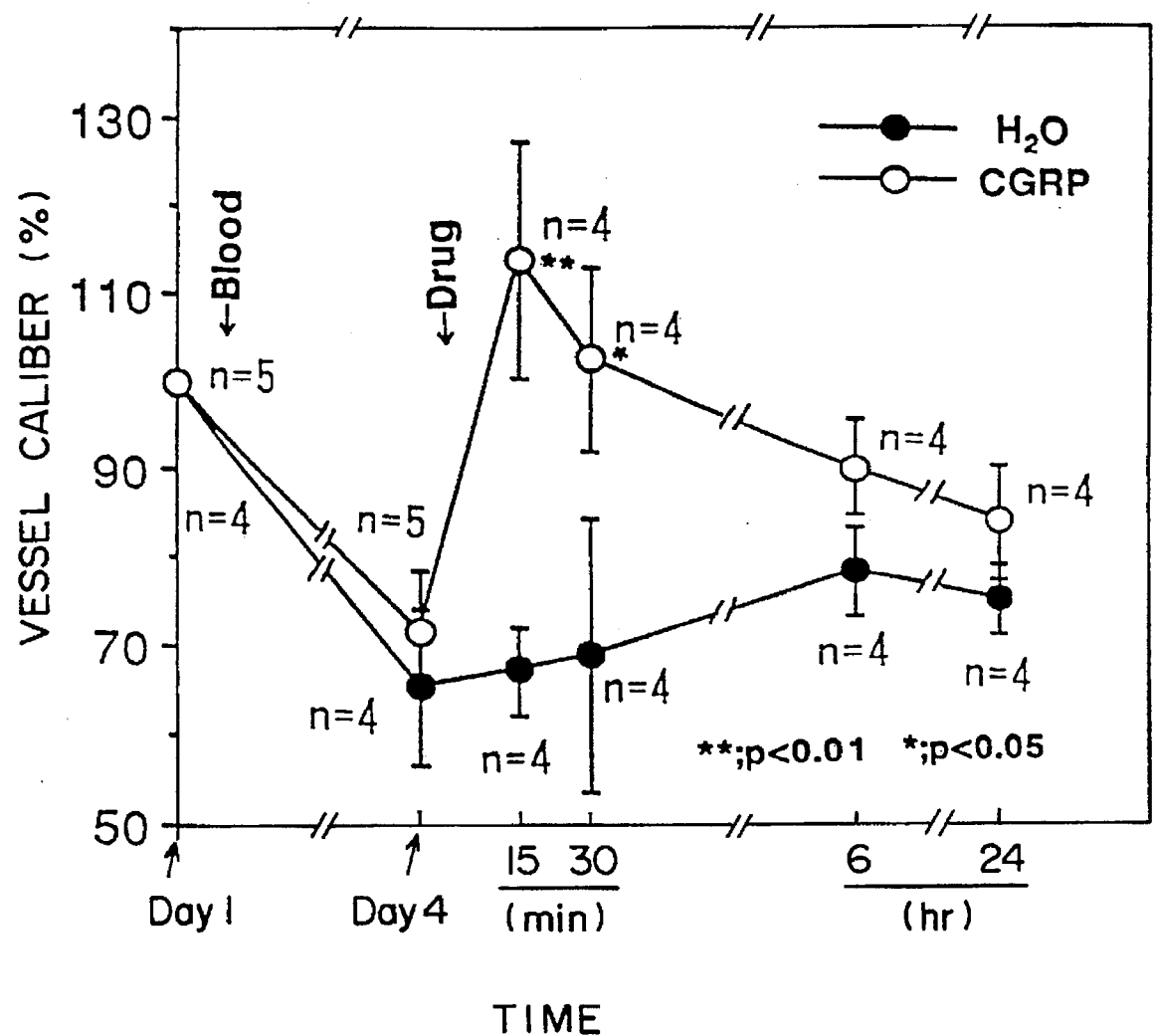
FIG. 13 shows the results of the vasodilative test by administration of the aqueous CGRP solution by the cisternal puncture method.

As another comparative example, portions of an aqueous CGRP solution or portions of distilled water were administered, respectively to rabbit models (2 animals about the aqueous CGRP solution and 4 animals about the distilled water) in which spasm of the basilar artery had been clearly observed after subarachnoid hemorrhage, also by a cisternal puncture method in accordance with the known method in the above (1), and the blood vessel calibers were measured in the same manner as in the Examples 36 and 37. The results are shown in FIG. 13.

Example 38

Vasodilative test (II)

Figure 14:
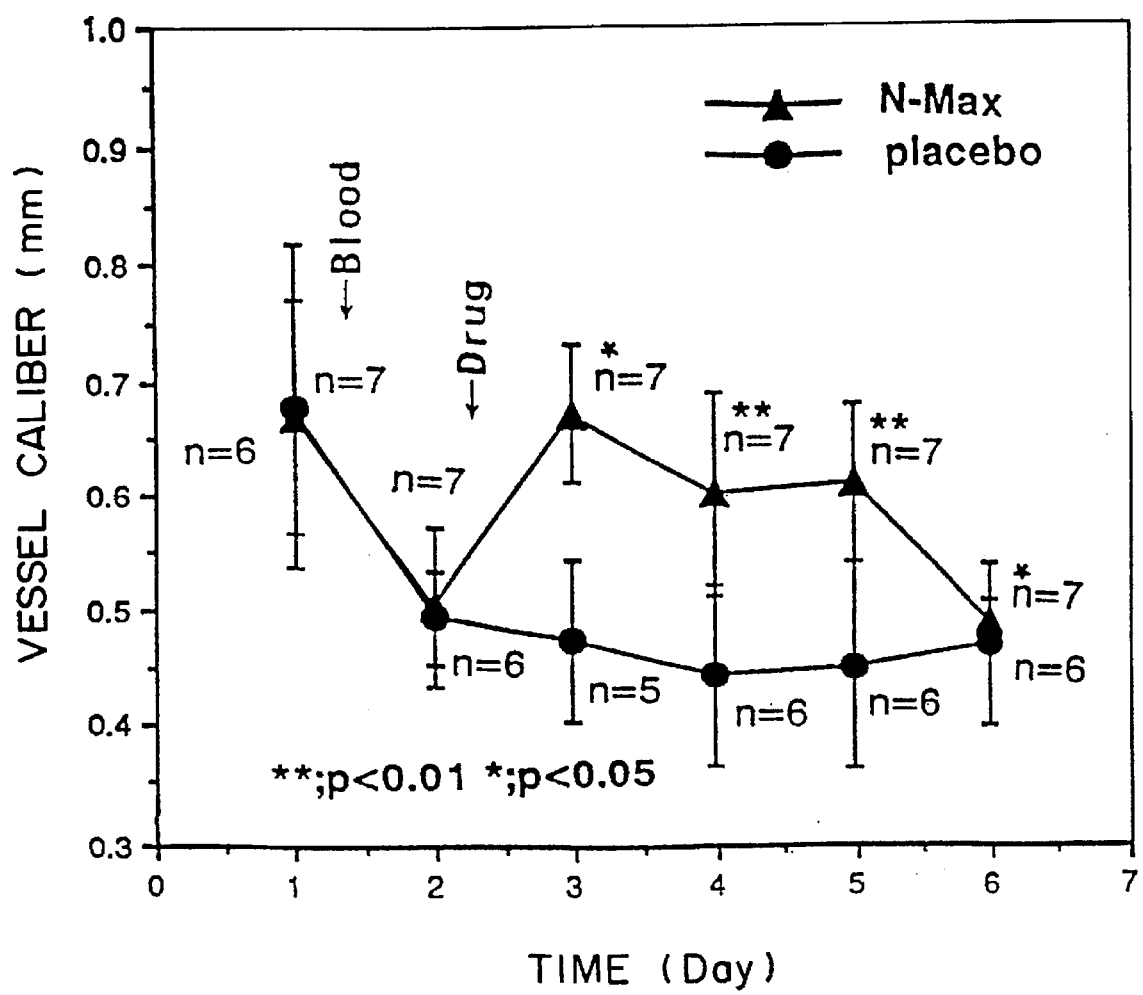
FIG. 14 shows the results of the vasodilative test similar to those in FIGS. 10 and 11, on a preparation of the invention, P-VIII (containing an N-terminus-modified maxadilan, SEQ ID NO: 3)

A vasodilative test was performed in the same manner as in Examples 36 and 37 using the tablet obtained in Example 8 (P-VIII) and a tablet (placebo tablet) not containing a GSIL-modified-type maxadilan denoted by SEQ ID NO: 3 as a physiologically active peptide. The results are shown in FIG. 14. The placebo tablet was prepared in the same manner as in Example 8 except for replacement of the GSIL-modified-type maxadilan by hydroxypropylcellulose.

Example 39

In vivo release test on a physiologically active substance

Figure 15:
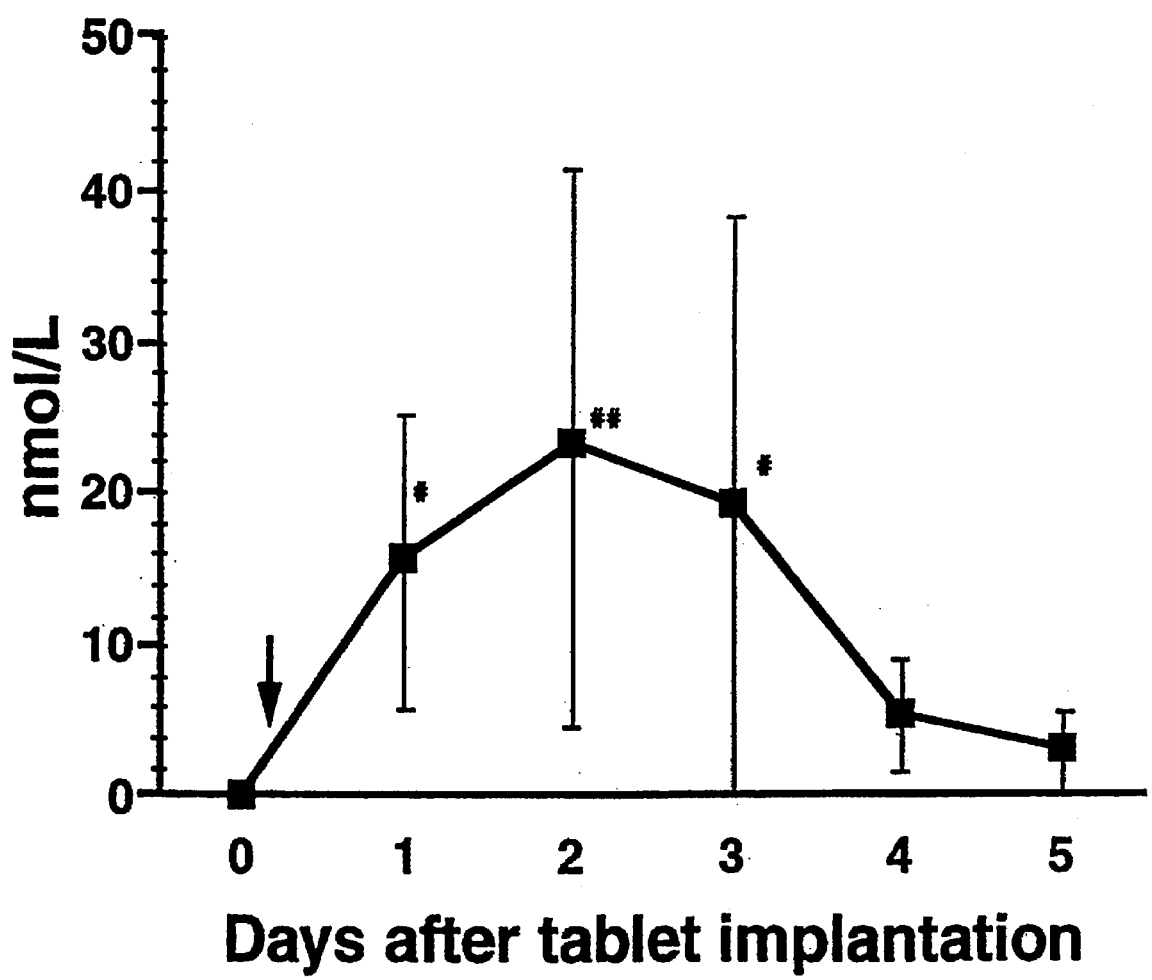
FIG. 15 is a graph showing the results of an in vitro release test on a preparation of the invention, P-II by change of the CGRP concentration in the CSF.

In addition to Example 35, this experiment was performed aiming to obtain statistically more meaningful data. The operations described in Example 35 were repeated except that 30 rabbits (5 animals each for Normal, day 1, day 2, day 3, day 4 and day 5) were used, and the cerebrospinal fluids (CSF) were collected 1 day (day 1), 2 days (day 2), 3 days (day 3), 4 days (day 4) and 5 days (day 5) after the implantation of the tablet (P-II) from 5 animals each for the respective days, and thereby the CGRP concentrations in the CSFs were assayed. The results are shown in FIG. 15.

In the above Normal means a case where the tablet (P-II) was not implanted.

Example 40

In vivo disappearance test on a pharmaceutical preparation

An in vivo test related to the disappearance effect of a prolonged releasing pharmaceutical preparation (tablet) in the brains was performed by the following method, using the tablet (P-II) obtained in Example 2. In this test, 18 rabbits (2 animals each for day 1, day 2, day 3, day 4, day 5, day 10, month 1, month 3 and month 6) were used. The operations and the results are shown below.

Method of implantation of the tablet into the brain

Each of 18 rabbits (2.5-3.0 kg) was anesthetized with sodium pentobarbital and fixed on its face, the occipital bone membrane (dura mater) was exposed by incision, and the occipital bone was shaved by a drill to expose the dura mater further wider. Thereafter, the dura mater and the arachnoidea were incised to a length of about 8 mm, the tablet of Example 2 as a prolonged releasing pharmaceutical preparation was implanted, the dura mater, the muscle and the skin were sutured, and an appropriate amount of an antibiotic was administered to the incision site.

Assay method and assessment criterion

On 1st day, 2nd day, 3rd day, 4th day, 5th day, 10th day, 1st month, 3rd month, 6th month after the implantation of the tablet into the rabbits, the two rabbits each for the respective days were subjected to a craniotomy operation to expose the portion where the tablet was implanted, and observation was performed visually. The assessment criterion was as follows.

- The tablet scarcely disappears
- Nearly half of the tablet disappeared
++ Almost all the tablet disappeared
+++ The tablet completely disappeared Test results

TABLE 2

| Days from the day when the tablets was implanted | Assessment of disappearance of the tablet |
| --- | --- |
| 1st day | − |
| 2nd day | − |
| 3rd day | −+ |
| 4th day | + |
| 5th day | + |
| 10th day | + |
| 1st month | ++ |
| 3rd month | +++ |
| 6th month | +++ |

There was not any rabbit at all which died during the term when the disappearance effect test on this prolonged releasing pharmaceutical preparation (tablet) was performed.

Example 41

Cerebral vasospasm inhibition test on maxadilan (SEQ ID NO: 3)

Preparation of a cerebral vasospasm model animal

A Japanese white rabbit (male, weighing 2-3 kg) was subjected to general anesthesia by injection of sodium pentobarbital through the auricular vein. After the rabbit was retained so as not to move, the surroundings of the punctured vein were disinfected with sterilized ethanol, a self-retaining needle was punctured into the vein, and immediately thereafter, a silicone-made extension tube equipped, at one end, with a three way cock connected at the two ways with 10-ml syringes each containing physiological saline and connected at the residual way with a 10-ml syringe containing sodium pentobarbital was connected to the self-retaining needle (when the blood vessel is thin, the blood vessel is stimulated by fingers to dilate it). After the connection, the physiological saline was flashed and it was confirmed that the needle was in the vein, and then, the sodium pentobarbital was injected into the rabbit so that the amount became 75 mg per kg of the weight of the rabbit. At this time, since the animal went under anesthesia within one minute, the respiratory tract was previously secured so as to make respiration possible.

Insertion of catheter (Seldinger's method)

The femoral region artery was exposed by incision of the femoral region, and a catheter was inserted into the vertebral artery from the exposed portion under transillumination, using a guide wire. Separately, 0.2 ml of heparin was injected so as to prevent formation of thrombus at the time of insertion of the catheter.

Angiography

A spot for angiography was determined by transillumination, the head was fast fixed, back flow of the blood was confirmed, and 0.8 ml of a contrast medium was injected under a certain pressure (2.3 kg/cm$^2$). At the time when 0.6 ml thereof was injected, a photograph of the blood vessel was taken.

Cisterna puncture

This procedure was performed in common when blood of a test preparation was injected into the rabbit.

The animal was placed on its face, and the head was leaned downward so as to make an angle of 30° against a horizontal plane. After the occipital bone was confirmed, the primary cervical vertebrae was confirmed, and a 26G butterfly needle was stuck at an angle of about 60° between them. When the needle hit the occipital bone, the needle was made vertical to 90°, and punctured further deeply. At this point of time, it was confirmed that the cerebrospinal fluid flew out by reducing pressure. The fresh blood of the artery was injected through this needle at a rate of 1 ml/min in an amount of 1 ml per kg of the weight of the rabbit. After the injection, back flow of the cerebrospinal fluid was again confirmed, and the rabbit was allowed to stand, leaving it intact, for 15 minutes or more. Photographs of the cerebral blood vessel of the animal were taken 3 days after the blood injection.

Administration of a test preparation

Groups of rabbits, one group consisting of 5 animals, were treated as mentioned above, and among them, rabbits were selected wherein when the basilar artery was divided, starting from the junction from the vertebral artery, into three equal parts, and the diameter at the middle point was measured, spasm occurred at a level of 18% or more. About the selected rabbits, portions of an aqueous solution of a modified-type maxadilan denoted by SE ID NO: 3 or portions of distilled water as a comparative example were administered 3 days after the injection of the blood, respectively. After the administration, angiography of the basilar artery was performed, on each rabbit, over the lapse of time, and the ratio of the diameter of the blood vessel to that before subarachnoid hemorrhage was investigated. As to the model animals, rabbits weighing 2.5–3.0 kg were used as follows: 8 animals in the modified-type maxadilan administration group and 4 animals in the sterile water administration group. The dose of the modified-type maxadilan was 7 µg per kg of the weight of the rabbit.

Figure 16:
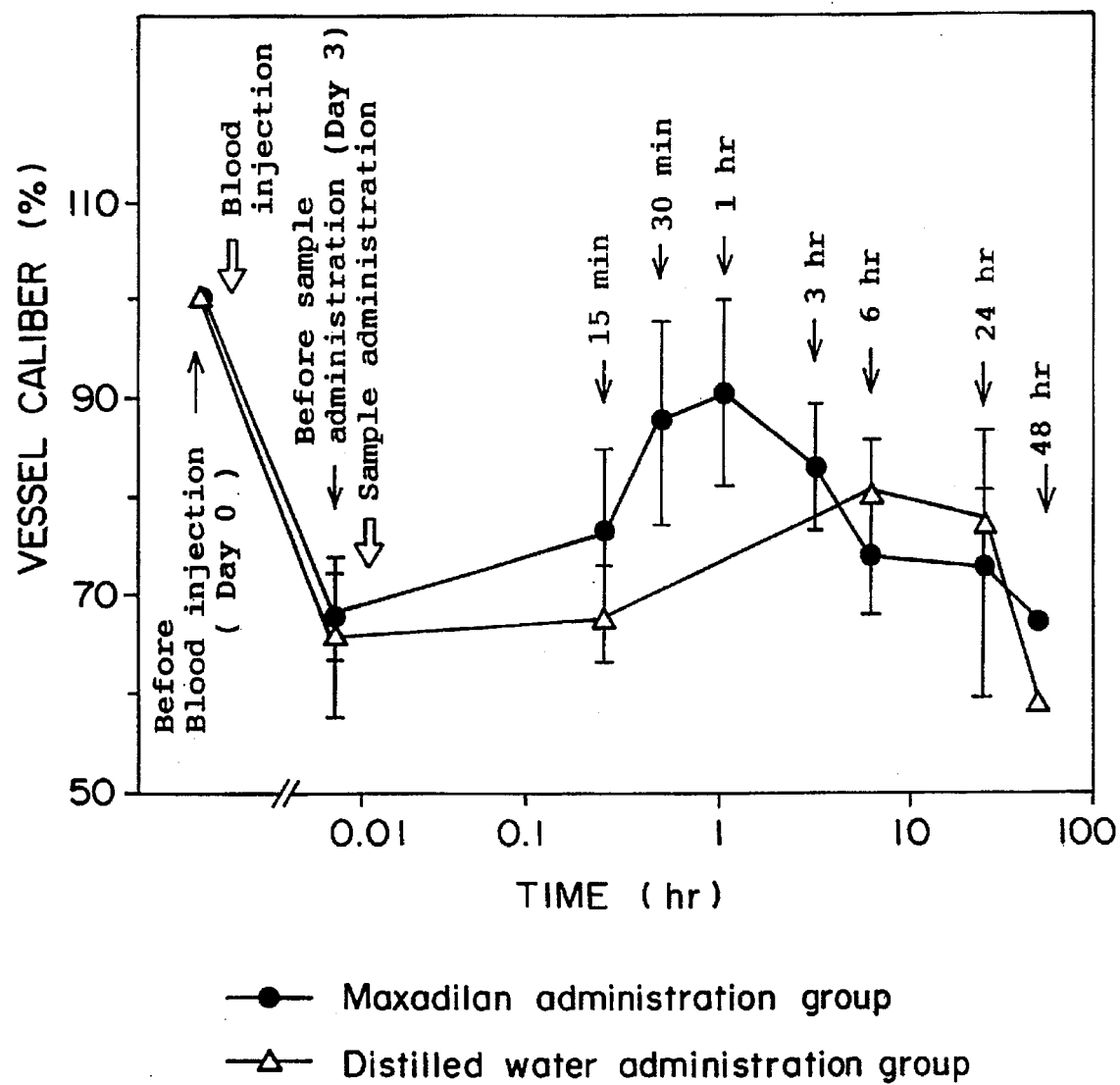
FIG. 16 is a graph showing the effect of inhibition of vasospasm when an aqueous solution of a modified-type maxadilan, SEQ ID NO: 3 was administered to a model animal of cerebral vasospasm by a cisternal puncture method.

The results are shown in FIG. 16.

As apparent from FIG. 16, in the aqueous modified-type maxadilan solution administration group, spasm was significantly inhibited during from immediately after the administration to about 4 hours thereafter, compared to the sterile water administration group.

What is claimed is:

1. A pharmaceutical preparation comprising a physiologically effective amount of a physiologically active substance and a carrier which provides a prolonged release of the physiologically active substance, wherein the carrier of the physiologically active substance comprises a combination of a cellulosic polymer selected from the group consisting of cellulose ethers and crystalline cellulose and at least one auxiliary component selected from fat and oils, waxes, fatty acids, saccharides and polyacrylate esters, wherein the carrier comprises at least 10 to 90% by weight of a cellulose ether and 1 to 40% by weight of a saccharide, based on the total weight of the pharmaceutical preparation, and wherein said preparation is suitable for intrathecal implantation.

2. A pharmaceutical preparation comprising a physiologically effective amount of a physiologically active substance and a carrier which provides a prolonged release of the physiologically active substance, wherein the carrier of the physiologically active substance comprises a combination of a cellulosic polymer selected from the group consisting of cellulose ethers and crystalline cellulose and at least one auxiliary component selected from fat and oils, waxes, fatty acids, saccharides and polyacrylate esters, wherein the carrier comprises at least 10 to 90% by weight of crystalline cellulose and 0.01 to 10% by weight of a polyacrylate ester, based on the total weight of the pharmaceutical preparation, and wherein said preparation is suitable for intrathecal implantation.

3. A pharmaceutical preparation comprising a physiologically effective amount of a physiologically active substance and a carrier which provides a prolonged release of the physiologically active substance, wherein the carrier of the physiologically active substance comprises a combination of a cellulosic polymer selected from the group consisting of cellulose ethers and crystalline cellulose and at least one auxiliary component selected from fat and oils, waxes, fatty acids, saccharides and polyacrylate esters, wherein the physiologically active substance is one or more substance selected from the group consisting of calcitonin gene-related peptide (CGRP) and maxadilans (MAXs), and wherein said preparation is suitable for intrathecal implantation.

4. The pharmaceutical preparation according to claim 3 wherein the carrier comprises 10 to 90 % by weight of a cellulose ether, 1 to 30% by weight of a fat or oil or a wax, and 1 to 30% by weight of a fatty acid, based on the total weight of the pharmaceutical preparation, and wherein the physiologically active peptide is a calcitonin gene-related peptide.

5. The pharmaceutical preparation according to claim 3 wherein the carrier comprises 10 to 90% by weight of a cellulose ether, 1 to 30% by weight of a fat or oil or a wax, and 1 to 30% by weight of a fatty acid, based on the total weight of the pharmaceutical preparation, and wherein the physiologically active peptide is a maxadilan.

6. The pharmaceutical preparation according to claim 2 wherein the physiologically active substance is a physiologically active peptide.

7. A pharmaceutical preparation according to claim 1 wherein the physiologically active substance is a physiologically active peptide.

8. A method for prophylaxis or treatment of cerebral vasospasm by use of a compound having a vasodilative action, which comprises a step of implanting a prolonged releasing pharmaceutical preparation comprising a vasodilative effective amount of the compound and a carrier which provides a prolonged release of the compound into a patient's brain in need of said treatment, wherein the compound is selected from the group consisting of CGRP, MAXs, deferoxamine, methylprednisolone, nicorandil, nicaraben, magnesium sulfate, actinomycin D, 21-aminosteroid, isoproterenol, tPA, nimodipine, hydrocortisone, nicardipine, nifedipine, diltiazem, dilazp, teprothid, AA861, papaverine, OKY 1581, amyl nitrite, erythrityl tetranitrate, isosorbide dinitrate, nitroglycerin, pentaerythritol tetranitrate, VIP, vasopressin, bradykinin, PACAP, SOD, catalase, bepridil, nadolol, felodipine, isradipine, verapamil, atenolol, metoprolol and propanolol.

9. A method for prophylaxis or treatment according to claim 8 wherein the carrier of the pharmaceutical preparation comprises 10 to 90% by weight of a cellulose ether and 1 to 40% by weight of a saccharide, based on the total weight of the pharmaceutical preparation; and the compound is selected from the group consisting of CGRP and MAXs.

10. A pharmaceutical preparation comprising a physiologically effective amount of a physiologically active substance and a carrier which provides a prolonged release of the physiologically active substance, wherein the physiologically active substance is one or more substance selected from the group consisting of CGRP and MAXs, and wherein the carrier of the physiologically active substance comprises 10 to 90% by weight of a cellulose ether, 1 to 30% by weight of a fat or oil or a wax, and 1 to 30% by weight of a fatty acid, based on the total weight of the pharmaceutical preparation.

11. A pharmaceutical preparation comprising a physiologically effective amount of a physiologically active substance and a carrier which provides a prolonged release of the physiologically active substance, wherein the physiologically active substance is one or more substance selected from the group consisting of CGRP and MAXs, and wherein the carrier of the physiologically active substance comprises 10 to 90% by weight of a cellulose ether, and 1 to 40% by weight of a saccharide, based on the total weight of the pharmaceutical preparation.

12. A pharmaceutical preparation comprising a physiologically effective amount of a physiologically active substance and a carrier which provides a prolonged release of the physiologically active substance, wherein the physiologically active substance is one or more substance selected from the group consisting of CGRP and MAXs, and wherein the carrier of the physiologically active substance is a combination of 10 to 90% by weight of a crystalline cellulose and 0.01 to 10% by weight of a polyacrylate ester with one or more substance selected from the group consisting of 1 to 30% by weight of a fatty acid, 1 to 30% by weight of a fat or an oil and 1 to 30% by weight of a wax, based on the total weight of the pharmaceutical preparation.

13. A pharmaceutical preparation comprising a physiologically effective amount of a physiologically active substance and a carrier which provides a prolonged release of the physiologically active substance, wherein the physiologically active substance is one or more substance selected from the group consisting of CGRP and MAXs, and wherein the carrier of the physiologically active substance comprises about 50% by weight of hyaluronic acid and about 50% by weight of a cationic polyacrylic acid derivative selected from poly(methyl methacrylate-co-butylmethacrylate-co-dimethylamino-ethyl methacrylate) and poly(ethyl acrylate-co-methyl methacrylate-co-trimethyl ammonium ethyl methacrylate hydrochloride), based on the total weight of the pharmaceutical preparation.

14. A method for prophylaxis or treatment of cerebral vasospasm which comprises administering an effective amount of at least one of MAXs into the body.

15. A method for prophylaxis or treatment according to claim 8 wherein the carrier of the pharmaceutical preparation comprises 10 to 90% by weight of crystalline cellulose and 0.01 to 10% by weight of a polyacrylate ester, based on the total weight of the pharmaceutical preparation; and the compound is selected from the group consisting of CGRP and MAXs.

16. A method for prophylaxis or treatment according to claim 8 wherein the carrier of the pharmaceutical preparation comprises about 50% by weight of hyaluronic acid and about 50% by weight of a cationic polyacrylic acid derivative selected from poly(methyl methacrylate-co-butylmethacrylate-co-dimethylamino-ethyl methacrylate) and poly(ethyl acrylate-co-methyl methacrylate-co-trimethyl ammonium ethyl methacrylate hydrochloride), based on the total weight of the pharmaceutical preparation; and the compound is selected from the group consisting of CGRP and MAXs.

17. A method for prophylaxis or treatment according to claim 8 wherein the compound is selected from the group consisting of CGRP and MAXs.

18. A method for prophylaxis or treatment according to claim 8 wherein the compound is CGRP.

19. A method for prophylaxis or treatment according to claim 8 wherein the compound is at least one of MAXs.

20. A method for prophylaxis or treatment according to claim 8 wherein the compound is a peptide having the amino acid sequence of SEQ ID NO: 3.

21. A method for prophylaxis or treatment according to claim 8 wherein the carrier of the prolonged releasing pharmaceutical preparation comprises a combination of a cellulosic polymer selected from the group consisting of cellulose ethers and crystalline cellulose and at least one auxiliary component selected from fats and oils, waxes, fatty acids, saccharides and polyacrylate esters.

22. A method for prophylaxis or treatment according to claim 8 wherein the carrier of the pharmaceutical preparation comprises 10 to 90% by weight of a cellulose ether, 1 to 30% by weight of a fat or oil or a wax, and 1 to 30% by weight of a fatty acid, based on the total weight of the pharmaceutical preparation.

23. A method for prophylaxis or treatment according to claim 8 wherein the carrier of the pharmaceutical preparation comprises 10 to 90% by weight of a cellulose ether and 1 to 40% by weight of a saccharide, based on the total weight of the pharmaceutical preparation.

24. A method for prophylaxis or treatment according to claim 8 wherein the carrier of the pharmaceutical preparation comprises 10 to 90% by weight of crystalline cellulose and 0.01 to 10% by weight of a polyacrylate ester, based on the total weight of the pharmaceutical preparation.

25. A method for prophylaxis or treatment according to claim 8 wherein the carrier of the pharmaceutical preparation comprises about 50% by weight of hyaluronic acid and about 50% by weight of a cationic polyacrylic acid derivative selected from poly(methyl methacrylate-co-butylmethacrylate-co-dimethylamino-ethyl methacrylate) and poly(ethyl acrylate-co-methyl methacrylate-co-trimethyl ammonium ethyl methacrylate hydrochloride), based on the total weight of the pharmaceutical preparation.

26. A method for prophylaxis or treatment according to claim 8 wherein the carrier of the pharmaceutical preparation comprises 10 to 90% by weight of a cellulose ether, 1 to 30% by weight of a fat or oil or a wax, and 1 to 30% by weight of a fatty acid, based on the total weight of the pharmaceutical preparation; and the compound is selected from the group consisting of CGRP and MAXs.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 63 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

```
Cys Asp Ala Thr Cys Gln Phe Arg Lys Ala Ile Asp Asp Cys Gln Lys
 1               5                  10                  15
Gln Ala His His Ser Asn Val Leu Gln Thr Ser Val Gln Thr Thr Ala
                20                  25                  30
Thr Phe Thr Ser Met Asp Thr Ser Gln Leu Pro Gly Asn Ser Val Phe
         35                  40                  45
Lys Glu Cys Met Lys Gln Lys Lys Glu Phe Lys Ala Gly Lys
     50                  55                  60
```

( 2 ) INFORMATION FOR SEQ ID NO:2:

( i ) SEQUENCE CHARACTERISTICS:
        ( A ) LENGTH: 66 amino acids
        ( B ) TYPE: amino acid
        ( C ) STRANDEDNESS: single
        ( D ) TOPOLOGY: linear ( i i ) MOLECULE TYPE: peptide (x i) SEQUENCE DESCRIPTION: SEQ ID NO:2:

| Gly | Ile | Leu | Cys | Asp | Ala | Thr | Cys | Gln | Phe | Arg | Lys | Ala | Ile | Asp | Asp |
|---|---|---|---|---|---|---|---|---|---|---|---|---|---|---|---|
| 1 | | | | 5 | | | | | 10 | | | | | 15 | |
| Cys | Gln | Lys | Gln | Ala | His | His | Ser | Asn | Val | Leu | Gln | Thr | Ser | Val | Gln |
| | | | 20 | | | | | 25 | | | | | 30 | | |
| Thr | Thr | Ala | Thr | Phe | Thr | Ser | Met | Asp | Thr | Ser | Gln | Leu | Pro | Gly | Asn |
| | | 35 | | | | | 40 | | | | | 45 | | | |
| Ser | Val | Phe | Lys | Glu | Cys | Met | Lys | Gln | Lys | Lys | Lys | Glu | Phe | Lys | Ala |
| | 50 | | | | | 55 | | | | | 60 | | | | |
| Gly | Lys |
| 65 | |

(2) INFORMATION FOR SEQ ID NO:3:

(i) SEQUENCE CHARACTERISTICS:
    (A) LENGTH: 67 amino acids
    (B) TYPE: amino acid
    (C) STRANDEDNESS: single
    (D) TOPOLOGY: linear (ii) MOLECULE TYPE: peptide (x i) SEQUENCE DESCRIPTION: SEQ ID NO:3:

| Gly | Ser | Ile | Leu | Cys | Asp | Ala | Thr | Cys | Gln | Phe | Arg | Lys | Ala | Ile | Asp |
|---|---|---|---|---|---|---|---|---|---|---|---|---|---|---|---|
| 1 | | | | 5 | | | | | 10 | | | | | 15 | |
| Asp | Cys | Gln | Lys | Gln | Ala | His | His | Ser | Asn | Val | Leu | Gln | Thr | Ser | Val |
| | | | 20 | | | | | 25 | | | | | 30 | | |
| Gln | Thr | Thr | Ala | Thr | Phe | Thr | Ser | Met | Asp | Thr | Ser | Gln | Leu | Pro | Gly |
| | | 35 | | | | | 40 | | | | | 45 | | | |
| Asn | Ser | Val | Phe | Lys | Glu | Cys | Met | Lys | Gln | Lys | Lys | Lys | Glu | Phe | Lys |
| | 50 | | | | | 55 | | | | | 60 | | | | |
| Ala | Gly | Lys |
| 65 | | |

(2) INFORMATION FOR SEQ ID NO:4:

(i) SEQUENCE CHARACTERISTICS:
    (A) LENGTH: 71 amino acids
    (B) TYPE: amino acid
    (C) STRANDEDNESS: single
    (D) TOPOLOGY: linear (ii) MOLECULE TYPE: peptide (x i) SEQUENCE DESCRIPTION: SEQ ID NO:4:

| Leu | Val | Pro | Arg | Gly | Ser | Ile | Leu | Cys | Asp | Ala | Thr | Cys | Gln | Phe | Arg |
|---|---|---|---|---|---|---|---|---|---|---|---|---|---|---|---|
| 1 | | | | 5 | | | | | 10 | | | | | 15 | |
| Lys | Ala | Ile | Asp | Asp | Cys | Gln | Lys | Gln | Ala | His | His | Ser | Asn | Val | Leu |
| | | | 20 | | | | | 25 | | | | | 30 | | |
| Gln | Thr | Ser | Val | Gln | Thr | Thr | Ala | Thr | Phe | Thr | Ser | Met | Asp | Thr | Ser |
| | | 35 | | | | | 40 | | | | | 45 | | | |
| Gln | Leu | Pro | Gly | Asn | Ser | Val | Phe | Lys | Glu | Cys | Met | Lys | Gln | Lys | Lys |
| | 50 | | | | | 55 | | | | | 60 | | | | |
| Lys | Glu | Phe | Lys | Ala | Gly | Lys |
| 65 | | | | | 70 | |